(12) United States Patent
Brasier et al.

(10) Patent No.: US 7,521,534 B1
(45) Date of Patent: Apr. 21, 2009

(54) IKK GAMMA GENE PRODUCTS AND METHODS FOR MAKING AND USING SAME

(75) Inventors: Allan R. Brasier, Galveston, TX (US); Tao Hai, Galveston, TX (US); Thomas G. Wood, Houston, TX (US); Yuanfen Wei, Galveston, TX (US)

(73) Assignee: The University Board of Regents of Texas System, Austin, TX (US)

( * ) Notice: Subject to any disclaimer, the term of this patent is extended or adjusted under 35 U.S.C. 154(b) by 157 days.

(21) Appl. No.: 10/793,339

(22) Filed: Mar. 3, 2004

Related U.S. Application Data

(60) Provisional application No. 60/451,546, filed on Mar. 3, 2003.

(51) Int. Cl.
C07K 1/00 (2006.01)
(52) U.S. Cl. ..................................... 530/350
(58) Field of Classification Search .................. 530/350; 435/194
See application file for complete search history.

(56) References Cited

U.S. PATENT DOCUMENTS

| | | | | |
|---|---|---|---|---|
| 6,171,781 | B1 * | 1/2001 | Crabtree et al. | 506/10 |
| 6,734,174 | B1 * | 5/2004 | Wallach et al. | 514/44 |
| 6,960,648 | B2 * | 11/2005 | Bonny | 530/330 |
| 2002/0086356 | A1 | 7/2002 | Tuschl et al. | |
| 2003/0119017 | A1 | 6/2003 | McSwiggen et al. | |
| 2004/0219615 | A1 * | 11/2004 | Wallach et al. | 435/7.23 |

FOREIGN PATENT DOCUMENTS

WO 01/75067 * 10/2001

OTHER PUBLICATIONS

Mirriam Webster's Collegiate Dictionary, 10th edition, 1997, p. 51.*
Morris et al., "Recovery of Cytopathogenic Agent from Chimpanzees with Coryza," *Proc. Soc. Exp. Biol. Med.*, 92(3):544-549 (1956).
Murphy, "The Molecular Biology of Leukocyte Chemoattractant Receptors," *Annu. Rev. Immunol.*, 12:593-633 (1994).
Jin et al., "Isolation of Full-Length cDNA and Chromosomal Localization of Human NF-kappaB Modulator NEMO to Xq28," *J. Biomed. Sci.*, 6(2):115-120 (1998).
Murphy et al., "Transcriptional Repression by Wild-type p53 Utilizes Histone Deacetylases, Mediated by Interaction with mSin3a," *Genes Dev.*, 13(19):2490-2501 (1999).
Sherman et al., "Role of Signal Transducers and Activators of Transcription 1 and -3 in Inducible Regulation of the Human Angiotensinogen Gene by Interleukin-6," *Mol. Endocrinol.*, 15(3):441-457 (2001).

* cited by examiner

*Primary Examiner*—Maryam Monshipouri
(74) *Attorney, Agent, or Firm*—Benjamin Aaron Adler

(57) ABSTRACT

Disclosed are isolated IKKγΔ; isolated nucleic acid molecules encoding IKKγΔ; expression vectors and cells which contain such nucleic acid molecules; oligonucleotides which are complementary to at least a portion of nucleic acid molecules encoding IKKγΔ but which are not complementary to any portion of nucleic acid molecules encoding wild type IKKγ; antibodies which are specific for IKKγΔ; DNA and RNA oligomers, optionally in labeled or enzymatically active form, which are capable of selectively hybridizing to nucleic acid molecules encoding IKKγΔ; and DNA and RNA oligomers, optionally in labeled or enzymatically active form, which are capable of selectively hybridizing to nucleic acid molecules encoding IKKγΔ but which do not hybridize with nucleic acid molecules encoding wild type IKKγ. Methods for using these materials to inhibit formation of IKKγΔ-containing IKK, to inhibit NF-κB activation, and to treat or prevent inflammation are also disclosed.

3 Claims, 7 Drawing Sheets

FIGURE 1

```
GAGGTCCCATCAGCCCTTGCCCTGTTGGATGAATAGGCACCTCTGGAAGAGCCAACTGTG
                                     M  N  R  H  L  W  K  S  Q  L  C

TGAGATGGTGCAGCCCAGTGGTGGCCCGGCAGCAGATCAGGACGTACTGGGCGAAGAGTC
 E  M  V  Q  P  S  G  G  P  A  A  D  Q  D  V  L  G  E  E  S

TCCTCTGGGGAAGCCAGCCATGCTGCACCTGCCTTCAGAACAGGGCGCTCCTGAGACCCT
 P  L  G  K  P  A  M  L  H  L  P  S  E  Q  G  A  P  E  T  L

CCAGCGCTGCCTGGAGGAGAATCAAGAGCTCCGAGATGCCATCCGGCAGAGCAACCAGAT
 Q  R  C  L  E  E  N  Q  E  L  R  D  A  I  R  Q  S  N  Q  I

TCTGCGGGAGCGCTGCGAGGAGCTTCTGCATTTCCAAGCCAGCCAGAGGGAGGAGAAGGA
 L  R  E  R  C  E  E  L  L  H  F  Q  A  S  Q  R  E  E  K  E

GTTCCTCATGTGCAAGTTCCAGGAGGCCAGGAAACTGGTGGAGAGACTCGGCCTGGAGAA
 F  L  M  C  K  F  Q  E  A  R  K  L  V  E  R  L  G  L  E  K

GCTCGATCTGAAGAGGCAGAAGGAGCAGGCTCTGCGGGAGGTGGAGCACCTGAAGAGATG
 L  D  L  K  R  Q  K  E  Q  A  L  R  E  V  E  H  L  K  R  C

CCAGCAGCAGATGGCTGAGGACAAGGCCTCTGTGAAAGCCCAGGTGACGTCCTTGCTCGG
 Q  Q  Q  M  A  E  D  K  A  S  V  K  A  Q  V  T  S  L  L  G

GGAGCTGCAGGAGAGCCAGAGTCGCTTGGAGGCTGCCACTAAGGAATGCCAGGCTCTGGA
 E  L  Q  E  S  Q  S  R  L  E  A  A  T  K  E  C  Q  A  L  E

GGGTCGGAGGAAGCTGGCCCAGTTGCAGGTGGCCTATCACCAGCTCTTCCAAGAATACGA
 G  R  R  K  L  A  Q  L  Q  V  A  Y  H  Q  L  F  Q  E  Y  D

CAACCACATCAAGAGCAGCGTGGTGGGCAGTGAGCGGAAGCGAGGAATGCAGCTGGAAGA
 N  H  I  K  S  S  V  V  G  S  E  R  K  R  G  M  Q  L  E  D

TCTCAAACAGCAGCTCCAGCAGGCCGAGGAGGCCCTGGTGGCCAAACAGGAGGTGATCGA
 L  K  Q  Q  L  Q  Q  A  E  E  A  L  V  A  K  Q  E  V  I  D

TAAGCTGAAGGAGGAGGCCGAGCAGCACAAGATTGTGATGGAGACCGTTCCGGTGCTGAA
 K  L  K  E  E  A  E  Q  H  K  I  V  M  E  T  V  P  V  L  K

GGCCCAGGCGGATATCTACAAGGCGGACTTCCAGGCTGAGAGGCAGGCCCGGGAGAAGCT
 A  Q  A  D  I  Y  K  A  D  F  Q  A  E  R  Q  A  R  E  K  L

GGCCGAGAAGAAGGAGCTCCTGCAGGAGCAGCTGGAGCAGCTGCAGAGGGAGTACAGCAA
 A  E  K  K  E  L  L  Q  E  Q  L  E  Q  L  Q  R  E  Y  S  K
```

FIGURE 1 (continued)

```
ACTGAAGGCCAGCTGTCAGGAGTCGGCCAGGATCGAGGACATGAGGAAGCGGCATGTCGA
  L  K  A  S  C  Q  E  S  A  R  I  E  D  M  R  K  R  H  V  E

GGTCTCCCAGGCCCCCTTGCCCCCGCCCCTGCCTACCTCTCCTCTCCCTGGCCCTGCC
  V  S  Q  A  P  L  P  P  A  P  A  Y  L  S  S  P  L  A  P

CAGCCAGAGGAGGAGCCCCCCCGAGGAGCCACCTGACTTCTGCTGTCCCAAGTGCCAGTA
  S  Q  R  R  S  P  P  E  E  P  P  D  F  C  C  P  K  C  Q  Y

TCAGGCCCCTGATATGGACACCCTGCAGATACATGTCATGGAGTGCATTGAGTAGGGCCG
  Q  A  P  D  M  D  T  L  Q  I  H  V  M  E  C  I  E  *
```

FIGURE 2

```
GAGGTCCCATCAGCCCTTGCCCTGTTGGATGAATAGGCACCTCTGGAAGAGCCAACTGTG
                                  M  N  R  H  L  W  K  S  Q  L  C

TGAGATGGTGCAGCCCAGTGGTGGCCCGGCAGCAGATCAGGACGTACTGGGCGAAGAGTC
 E  M  V  Q  P  S  G  G  P  A  A  D  Q  D  V  L  G  E  E  S

TCCTCTGGGGAAGCCAGCCATGCTGCACCTGCCTTCAGAACAGGGCGCTCCTGAGACCCT
  P  L  G  K  P  A  M  L  H  L  P  S  E  Q  G  A  P  E  T  L

CCAGCGCTGCCTGGAGGAGAATCAAGAGCTCCGAGATGCCATCCGGCAGAGCAACCAGAT
  Q  R  C  L  E  E  N  Q  E  L  R  D  A  I  R  Q  S  N  Q  I

TCTGCGGGAGCGCTGCGAGGAGCTTCTGCATTTCCAAGCCAGCCAGAGGGAGGAGAAGGA
  L  R  E  R  C  E  E  L  L  H  F  Q  A  S  Q  R  E  E  K  E

GTTCCTCATGTGCAAGTTCCAGGAGGCCAGGAAACTGGTGGAGAGACTCGGCCTGGAGAA
  F  L  M  C  K  F  Q  E  A  R  K  L  V  E  R  L  G  L  E  K

GCTCGATCTGAAGAGGCAGAAGGAGCAGGCTCTGCGGGAGGTGGAGCACCTGAAGAGATG
  L  D  L  K  R  Q  K  E  Q  A  L  R  E  V  E  H  L  K  R  C

CCAGCAGCAGATGGCTGAGGACAAGGCCTCTGTGAAAGCCCAGGTGACGTCCTTGCTCGG
  Q  Q  Q  M  A  E  D  K  A  S  V  K  A  Q  V  T  S  L  L  G

GGAGCTGCAGGAGAGCCAGAGTCGCTTGGAGGCTGCCACTAAGGAATGCCAGGCTCTGGA
  E  L  Q  E  S  Q  S  R  L  E  A  A  T  K  E  C  Q  A  L  E

GGGTCGGGCCCGGGCGGCCAGCGAGCAGGCGCGGCAGCTGGAGAGTGAGCGCGAGGCGCT
  G  R  A  R  A  A  S  E  Q  A  R  Q  L  E  S  E  R  E  A  L

GCAGCAGCAGCACAGCGTGCAGGTGGACCAGCTGCGCATGCAGGGCCAGAGCGTGGAGGC
  Q  Q  Q  H  S  V  Q  V  D  Q  L  R  M  Q  G  Q  S  V  E  A

CGCGCTCCGCATGGAGCGCCAGGCCGCCTCGGAGGAGAAGAGGAAGCTGGCCCAGTTGCA
  A  L  R  M  E  R  Q  A  A  S  E  E  K  R  K  L  A  Q  L  Q

GGTGGCCTATCACCAGCTCTTCCAAGAATACGACAACCACATCAAGAGCAGCGTGGTGGG
  V  A  Y  H  Q  L  F  Q  E  Y  D  N  H  I  K  S  S  V  V  G

CAGTGAGCGGAAGCGAGGAATGCAGCTGGAAGATCTCAAACAGCAGCTCCAGCAGGCCGA
  S  E  R  K  R  G  M  Q  L  E  D  L  K  Q  Q  L  Q  Q  A  E

GGAGGCCCTGGTGGCCAAACAGGAGGTGATCGATAAGCTGAAGGAGGAGGCCGAGCAGCA
  E  A  L  V  A  K  Q  E  V  I  D  K  L  K  E  E  A  E  Q  H

CAAGATTGTGATGGAGACCGTTCCGGTGCTGAAGGCCCAGGCGGATATCTACAAGGCGGA
  K  I  V  M  E  T  V  P  V  L  K  A  Q  A  D  I  Y  K  A  D
```

FIGURE 2 (continued)

```
CTTCCAGGCTGAGAGGCAGGCCCGGGAGAAGCTGGCCGAGAAGAAGGAGCTCCTGCAGGA
  F  Q  A  E  R  Q  A  R  E  K  L  A  E  K  K  E  L  L  Q  E

GCAGCTGGAGCAGCTGCAGAGGGAGTACAGCAAACTGAAGGCCAGCTGTCAGGAGTCGGC
  Q  L  E  Q  L  Q  R  E  Y  S  K  L  K  A  S  C  Q  E  S  A

CAGGATCGAGGACATGAGGAAGCGGCATGTCGAGGTCTCCCAGGCCCCCTTGCCCCCCGC
  R  I  E  D  M  R  K  R  H  V  E  V  S  Q  A  P  L  P  P  A

CCCTGCCTACCTCTCCTCTCCCCTGGCCCTGCCCAGCCAGAGGAGGAGCCCCCCCGAGGA
  P  A  Y  L  S  S  P  L  A  L  P  S  Q  R  R  S  P  P  E  E

GCCACCTGACTTCTGCTGTCCCAAGTGCCAGTATCAGGCCCCTGATATGGACACCCTGCA
  P  P  D  F  C  C  P  K  C  Q  Y  Q  A  P  D  M  D  T  L  Q

GATACATGTCATGGAGTGCATTGAGTAGGGCCGGCCAGTGCAAGGCCACTGCCTGCCCGA
  I  H  V  M  E  C  I  E  *
```

FIGURE 3

```
IKKγ    GAGGCTGCCACTAAGGAATGCCAGGCTCTGGAGGGTCGGGCCCGGGCGGCCAGCGAGCAG    540
ΔIKKγ   GAGGCTGCCACTAAGGAATGCCAGGCTCTGGAGGGTCG........................    518

IKKγ    GCGCGGCAGCTGGAGAGTGAGCGCGAGGCGCTGCAGCAGCAGCACAGCGTGCAGGTGGAC    600
ΔIKKγ   ............................................................    518

IKKγ    CAGCTGCGCATGCAGGGCCAGAGCGTGGAGGCCGCGCTCCGCATGGAGCGCCAGGCCGCC    660
ΔIKKγ   ............................................................    518

IKKγ    TCGGAGGAGAAGAGGAAGCTGGCCCAGTTGCAGGTGGCCTATCACCAGCTCTTCCAAGAA    720
ΔIKKγ   ..........GAGGAAGCTGGCCCAGTTGCAGGTGGCCTATCACCAGCTCTTCCAAGAA    567
```

FIGURE 4

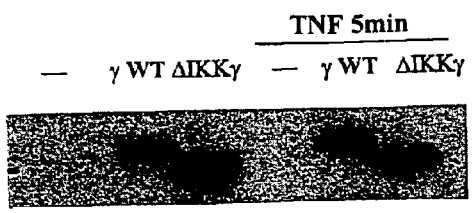

FIGURE 5

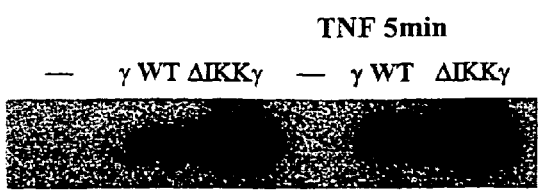

FIGURE 6

```
                            SEQUENCE LISTING

<160> NUMBER OF SEQ ID NOS: 16

<210> SEQ ID NO 1
<211> LENGTH: 368
<212> TYPE: PRT
<213> ORGANISM: Homo sapiens

<400> SEQUENCE: 1

Met Asn Arg His Leu Trp Lys Ser Gln Leu Cys Glu Met Val Gln Pro
1               5                   10                  15

Ser Gly Gly Pro Ala Ala Asp Gln Asp Val Leu Gly Glu Glu Ser Pro
            20                  25                  30

Leu Gly Lys Pro Ala Met Leu His Leu Pro Ser Glu Gln Gly Ala Pro
        35                  40                  45

Glu Thr Leu Gln Arg Cys Leu Glu Glu Asn Gln Glu Leu Arg Asp Ala
    50                  55                  60

Ile Arg Gln Ser Asn Gln Ile Leu Arg Glu Arg Cys Glu Glu Leu Leu
65                  70                  75                  80
```

```
His Phe Gln Ala Ser Gln Arg Glu Glu Lys Glu Phe Leu Met Cys Lys
                85                  90                  95
Phe Gln Glu Ala Arg Lys Leu Val Glu Arg Leu Gly Leu Glu Lys Leu
            100                 105                 110
Asp Leu Lys Arg Gln Lys Glu Gln Ala Leu Arg Glu Val Glu His Leu
        115                 120                 125
Lys Arg Cys Gln Gln Gln Met Ala Glu Asp Lys Ala Ser Val Lys Ala
    130                 135                 140
Gln Val Thr Ser Leu Leu Gly Glu Leu Gln Glu Ser Gln Ser Arg Leu
145                 150                 155                 160
Glu Ala Ala Thr Lys Glu Cys Gln Ala Leu Glu Gly Arg Arg Lys Leu
                165                 170                 175
Ala Gln Leu Gln Val Ala Tyr His Gln Leu Phe Gln Glu Tyr Asp Asn
            180                 185                 190
His Ile Lys Ser Ser Val Val Gly Ser Glu Arg Lys Arg Gly Met Gln
        195                 200                 205
Leu Glu Asp Leu Lys Gln Gln Leu Gln Gln Ala Glu Glu Ala Leu Val
    210                 215                 220
Ala Lys Gln Glu Val Ile Asp Lys Leu Lys Glu Ala Glu Gln His
225                 230                 235                 240
Lys Ile Val Met Glu Thr Val Pro Val Leu Lys Ala Gln Ala Asp Ile
                245                 250                 255
Tyr Lys Ala Asp Phe Gln Ala Glu Arg Gln Ala Arg Glu Lys Leu Ala
            260                 265                 270
Glu Lys Lys Glu Leu Leu Gln Glu Gln Leu Glu Gln Leu Gln Arg Glu
        275                 280                 285
Tyr Ser Lys Leu Lys Ala Ser Cys Gln Glu Ser Ala Arg Ile Glu Asp
    290                 295                 300
Met Arg Lys Arg His Val Glu Val Ser Gln Ala Pro Leu Pro Pro Ala
305                 310                 315                 320
Pro Ala Tyr Leu Ser Ser Pro Leu Ala Leu Pro Ser Gln Arg Arg Ser
                325                 330                 335
Pro Pro Glu Glu Pro Pro Asp Phe Cys Cys Pro Lys Cys Gln Tyr Gln
            340                 345                 350
Ala Pro Asp Met Asp Thr Leu Gln Ile His Val Met Glu Cys Ile Glu
        355                 360                 365

<210> SEQ ID NO 2
<211> LENGTH: 1140
<212> TYPE: DNA
<213> ORGANISM: Homo sapiens

<400> SEQUENCE: 2
gaggtcccat cagcccttgc cctgttggat gaataggcac ctctggaaga gccaactgtg      60
tgagatggtg cagcccagtg gtggcccggc agcagatcag gacgtactgg gcgaagagtc     120
tcctctgggg aagccagcca tgctgcacct gccttcagaa cagggcgctc ctgagaccct     180
ccagcgctgc ctggaggaga atcaagagct ccgagatgcc atccggcaga gcaaccagat     240
tctgcgggag cgctgcgagg agcttctgca tttccaagcc agccagaggg aggagaagga     300
gttcctcatg tgcaagttcc aggaggccag gaaactggtg gagagactcg gcctggagaa     360
gctcgatctg aagaggcaga aggagcaggc tctgcgggag gtggagcacc tgaagagatg     420
ccagcagcag atggctgagg acaaggcctc tgtgaaagcc aggtgacgt ccttgctcgg      480
ggagctgcag gagagccaga gtcgcttgga ggctgccact aaggaatgcc aggctctgga     540
```

```
gggtcggagg aagctggccc agttgcaggt ggcctatcac cagctcttcc aagaatacga    600
caaccacatc aagagcagcg tggtgggcag tgagcggaag cgaggaatgc agctggaaga    660
tctcaaacag cagctccagc aggccgagga ggccctggtg ccaaacagg  aggtgatcga    720 taagctgaag gaggaggccg agcagcacaa gattgtgatg gagaccgttc cggtgctgaa    780
ggcccaggcg gatatctaca aggcggactt ccaggctgag aggcaggccc gggagaagct    840
ggccgagaag aaggagctcc tgcaggagca gctggagcag ctgcagaggg agtacagcaa    900
actgaaggcc agctgtcagg agtcggccag gatcgaggac atgaggaagc ggcatgtcga    960
ggtctcccag gccccttgc  ccccgcccc  tgcctacctc tcctctcccc tggccctgcc   1020
cagccagagg aggagccccc ccgaggagcc acctgacttc tgctgtccca agtgccagta   1080
tcaggcccct gatatggaca ccctgcagat acatgtcatg gagtgcattg agtagggccg   1140
```

```
<210> SEQ ID NO 3
<211> LENGTH: 3
<212> TYPE: PRT
<213> ORGANISM: Homo sapiens

<400> SEQUENCE: 3

Gly Arg Arg
1

<210> SEQ ID NO 4
<211> LENGTH: 3
<212> TYPE: PRT
<213> ORGANISM: Homo sapiens

<400> SEQUENCE: 4

Arg Arg Lys
1

<210> SEQ ID NO 5
<211> LENGTH: 4
<212> TYPE: PRT
<213> ORGANISM: Homo sapiens

<400> SEQUENCE: 5

Gly Arg Arg Lys
1

<210> SEQ ID NO 6
<211> LENGTH: 6
<212> TYPE: PRT
<213> ORGANISM: Homo sapiens

<400> SEQUENCE: 6

Glu Gly Arg Arg Lys Leu
1               5

<210> SEQ ID NO 7
<211> LENGTH: 8
<212> TYPE: PRT
<213> ORGANISM: Homo sapiens

<400> SEQUENCE: 7

Leu Glu Gly Arg Arg Lys Leu Ala
1               5

<210> SEQ ID NO 8
<211> LENGTH: 419
```

<212> TYPE: PRT
<213> ORGANISM: Homo sapiens

<400> SEQUENCE: 8

```
Met Asn Arg His Leu Trp Lys Ser Gln Leu Cys Glu Met Val Gln Pro
1               5                   10                  15

Ser Gly Gly Pro Ala Ala Asp Gln Asp Val Leu Gly Glu Glu Ser Pro
            20                  25                  30

Leu Gly Lys Pro Ala Met Leu His Leu Pro Ser Glu Gln Gly Ala Pro
        35                  40                  45

Glu Thr Leu Gln Arg Cys Leu Glu Glu Asn Gln Glu Leu Arg Asp Ala
50                  55                  60

Ile Arg Gln Ser Asn Gln Ile Leu Arg Glu Arg Cys Glu Glu Leu Leu
65                  70                  75                  80

His Phe Gln Ala Ser Gln Arg Glu Glu Lys Glu Phe Leu Met Cys Lys
                85                  90                  95

Phe Gln Glu Ala Arg Lys Leu Val Glu Arg Leu Gly Leu Glu Lys Leu
            100                 105                 110

Asp Leu Lys Arg Gln Lys Glu Gln Ala Leu Arg Glu Val Glu His Leu
        115                 120                 125

Lys Arg Cys Gln Gln Gln Met Ala Glu Asp Lys Ala Ser Val Lys Ala
130                 135                 140

Gln Val Thr Ser Leu Leu Gly Glu Leu Gln Glu Ser Gln Ser Arg Leu
145                 150                 155                 160

Glu Ala Ala Thr Lys Glu Cys Gln Ala Leu Glu Gly Arg Ala Arg Ala
                165                 170                 175

Ala Ser Glu Gln Ala Arg Gln Leu Glu Ser Glu Arg Glu Ala Leu Gln
            180                 185                 190

Gln Gln His Ser Val Gln Val Asp Gln Leu Arg Met Gln Gly Gln Ser
        195                 200                 205

Val Glu Ala Ala Leu Arg Met Glu Arg Gln Ala Ala Ser Glu Glu Lys
210                 215                 220

Arg Lys Leu Ala Gln Leu Gln Val Ala Tyr His Gln Leu Phe Gln Glu
225                 230                 235                 240

Tyr Asp Asn His Ile Lys Ser Ser Val Val Gly Ser Glu Arg Lys Arg
                245                 250                 255

Gly Met Gln Leu Glu Asp Leu Lys Gln Gln Leu Gln Gln Ala Glu Glu
            260                 265                 270

Ala Leu Val Ala Lys Gln Glu Val Ile Asp Lys Leu Lys Glu Glu Ala
        275                 280                 285

Glu Gln His Lys Ile Val Met Glu Thr Val Pro Val Leu Lys Ala Gln
290                 295                 300

Ala Asp Ile Tyr Lys Ala Asp Phe Gln Ala Glu Arg Gln Ala Arg Glu
305                 310                 315                 320

Lys Leu Ala Glu Lys Lys Glu Leu Leu Gln Glu Leu Gln Leu
                325                 330                 335

Gln Arg Glu Tyr Ser Lys Leu Lys Ala Ser Cys Gln Gly Ser Ala Arg
            340                 345                 350

Ile Glu Asp Met Arg Lys Arg His Val Glu Val Ser Gln Ala Pro Leu
        355                 360                 365

Pro Pro Ala Pro Ala Tyr Leu Ser Ser Pro Leu Ala Leu Pro Ser Gln
370                 375                 380

Arg Arg Ser Pro Pro Glu Glu Pro Pro Asp Phe Cys Cys Pro Lys Cys
385                 390                 395                 400
```

Gln Tyr Gln Ala Pro Asp Met Asp Thr Leu Gln Ile His Val Met Glu
              405                 410                 415

Cys Ile Glu

<210> SEQ ID NO 9
<211> LENGTH: 1320
<212> TYPE: DNA
<213> ORGANISM: Homo sapiens

<400> SEQUENCE: 9

| | | | | | | |
|---|---|---|---|---|---|---|
| gaggtcccat | cagcccttgc | cctgttggat | gaataggcac | ctctggaaga | gccaactgtg | 60 |
| tgagatggtg | cagcccagtg | gtggcccggc | agcagatcag | gacgtactgg | gcgaagagtc | 120 |
| tcctctgggg | aagccagcca | tgctgcacct | gccttcagaa | cagggcgctc | ctgagaccct | 180 |
| ccagcgctgc | ctggaggaga | atcaagagct | ccgagatgcc | atccggcaga | gcaaccagat | 240 |
| tctgcgggag | cgctgcgagg | agcttctgca | tttccaagcc | agccagaggg | aggagaagga | 300 |
| gttcctcatg | tgcaagttcc | aggaggccag | gaaactggtg | gagagactcg | gcctggagaa | 360 |
| gctcgatctg | aagaggcaga | aggagcaggc | tctgcgggag | gtggagcacc | tgaagagatg | 420 |
| ccagcagcag | atggctgagg | acaaggcctc | tgtgaaagcc | caggtgacgt | ccttgctcgg | 480 |
| ggagctgcag | gagagccaga | gtcgcttgga | ggctgccact | aaggaatgcc | aggctctgga | 540 |
| gggtcgggcc | cggcggcca | gcgagcaggc | gcggcagctg | gagagtgagc | gcgaggcgct | 600 |
| gcagcagcag | cacagcgtgc | aggtggacca | gctgcgcatg | cagggccaga | gcgtggaggc | 660 |
| cgcgctccgc | atggagcgcc | aggccgcctc | ggaggagaag | aggaagctgg | cccagttgca | 720 |
| ggtggcctat | caccagctct | ccaagaata | cgacaaccac | atcaagagca | gcgtggtggg | 780 |
| cagtgagcgg | aagcgaggaa | tgcagctgga | agatctcaaa | cagcagctcc | agcaggccga | 840 |
| ggaggccctg | gtggccaaac | aggaggtgat | cgataagctg | aaggaggagg | ccgagcagca | 900 |
| caagattgtg | atggagaccg | ttccggtgct | gaaggcccag | gcggatatct | acaaggcgga | 960 |
| cttccaggct | gagaggcagg | cccggggagaa | gctggccgag | aagaaggagc | tcctgcagga | 1020 |
| gcagctggag | cagctgcaga | gggagtacag | caaactgaag | gccagctgtc | aggagtcggc | 1080 |
| caggatcgag | gacatgagga | gcggcatgt | cgaggtctcc | caggcccct | tgccccccgc | 1140 |
| ccctgcctac | ctctcctctc | ccctggccct | gcccagccag | aggaggagcc | ccccgagga | 1200 |
| gccacctgac | ttctgctgtc | caagtgcca | gtatcaggcc | cctgatatgg | acaccctgca | 1260 |
| gatacatgtc | atggagtgca | ttgagtaggg | ccggccagtg | caaggccact | gcctgcccga | 1320 |

<210> SEQ ID NO 10
<211> LENGTH: 51
<212> TYPE: PRT
<213> ORGANISM: Homo sapiens

<400> SEQUENCE: 10

Ala Arg Ala Ala Ser Glu Gln Ala Arg Gln Leu Glu Ser Glu Arg Glu
1               5                   10                  15

Ala Leu Gln Gln Gln His Ser Val Gln Val Asp Gln Leu Arg Met Gln
                20                  25                  30

Gly Gln Ser Val Glu Ala Ala Leu Arg Met Glu Arg Gln Ala Ala Ser
            35                  40                  45

Glu Glu Lys
    50

<210> SEQ ID NO 11
<211> LENGTH: 240
<212> TYPE: DNA
<213> ORGANISM: Homo sapiens

<400> SEQUENCE: 11
gaggctgcca ctaaggaatg ccaggctctg gagggtcggg cccggcggc cagcgagcag      60 gcgcggcagc tggagagtga gcgcgaggcg ctgcagcagc agcacagcgt gcaggtggac     120
cagctgcgca tgcagggcca gagcgtggag gccgcgctcc gcatggagcg ccaggccgcc    180
tcggaggaga agaggaagct ggcccagttg caggtggcct atcaccagct cttccaagaa    240

<210> SEQ ID NO 12
<211> LENGTH: 87
<212> TYPE: DNA
<213> ORGANISM: Homo sapiens

<400> SEQUENCE: 12
gaggctgcca ctaaggaatg ccaggctctg gagggtcgga ggaagctggc ccagttgcag     60
gtggcctatc accagctctt ccaagaa                                         87

<210> SEQ ID NO 13
<211> LENGTH: 18
<212> TYPE: DNA
<213> ORGANISM: Artificial sequence
<220> FEATURE:
<223> OTHER INFORMATION: Chemically synthesized

<400> SEQUENCE: 13
ggatccaacg ctgacgtc                                                   18

<210> SEQ ID NO 14
<211> LENGTH: 44
<212> TYPE: DNA
<213> ORGANISM: Artificial sequence
<220> FEATURE:
<223> OTHER INFORMATION: Chemically synthesized

<400> SEQUENCE: 14
gcaagcttag atctgtggtc tcatacagaa cttataagat tccc                      44

<210> SEQ ID NO 15
<211> LENGTH: 54
<212> TYPE: DNA
<213> ORGANISM: Artificial sequence
<220> FEATURE:
<223> OTHER INFORMATION: Chemically synthesized

<400> SEQUENCE: 15
gatccccttc ctccctgatg aggccgaaag gccgaaaccc tcctttttg gaaa            54

<210> SEQ ID NO 16
<211> LENGTH: 53
<212> TYPE: DNA
<213> ORGANISM: Artificial sequence
<220> FEATURE:
<223> OTHER INFORMATION: Chemically synthesized

<400> SEQUENCE: 16
agcttttcca aaaaggaggg tttcggcctt tcggcctcat cagggaggaa ggg             53

IKK GAMMA GENE PRODUCTS AND METHODS FOR MAKING AND USING SAME

The present application claims the benefit of U.S. Provisional Patent Application Ser. No. 60/451,546, filed Mar. 3, 2003, which provisional patent application is hereby incorporated by reference.

Each of the references cited in the present invention is hereby incorporated, in its entirety, by reference.

The present invention was made with the support of the National Institutes of Health Grant No. HL55630. The Federal Government may have certain rights in this invention.

FIELD OF THE INVENTION

The present invention relates, generally, to molecular biology and biochemistry and, more specifically, to products of the IKKγ gene and to methods for making and using such products.

BACKGROUND OF THE INVENTION

Nuclear factor κB ("NF-κB") is a family of inducible transcription factors controlling expression of genes that play important roles in airway inflammation and other inflammatory conditions and diseases, atherosclerosis, blood pressure, and immune response.

Under normal conditions, the NF-κB complex is inactivated in the cytoplasm by binding inhibitors of NF-κB. These inhibitors of NF-κB are referred to as "IκB". Upon cellular stimulation, for example, with angiotensin II, oxidized low-density lipoproteins, cytokines, or viral pathogens, IκB is phosphorylated and degraded, liberating NF-κB, which enters the nucleus and activates the expression of target genes.

IκB Kinase ("IKK") is a multisubunit complex that transduces upstream activating signals into the rate-limiting phosphorylation of IκB. More particularly, IKK is composed of 10-12 proteins whose composition is largely unknown. These proteins include catalytic kinases, such as IKKα and IKKβ; regulatory proteins, such as NF-κB essential modulator, which is sometimes referred to as "NEMO", and IKKγ; and scaffolding proteins, such as IKAP.

Several studies have demonstrated that IKK is required for NF-κB activation. For example, one such study demonstrated that specific peptide inhibitors of IKK block inflammation in mice challenged with lipopolysaccharide ("LPS").

In view of the above, a need remains for methods and products which can modulate NF-κB activation and, thus, which can be used in the treatment, prevention, or management of inflammatory conditions and diseases and of other conditions, diseases, and processes in which activated NF-κB plays a direct or indirect role. The present invention is directed, in part, to addressing this need.

SUMMARY OF THE INVENTION

The present invention relates to an isolated polypeptide having an amino acid sequence corresponding to SEQ ID NO:1.

The present invention also relates to an isolated nucleic acid molecule encoding a polypeptide having an amino acid sequence corresponding to SEQ ID NO:1.

The present invention also relates to an antibody or fragment thereof specific for a polypeptide having an amino acid sequence corresponding to SEQ ID NO:1.

The present invention also relates to an isolated polypeptide having an amino acid sequence corresponding to an antigenic portion of SEQ ID NO:1, wherein the isolated polypeptide comprises an amino acid sequence corresponding to either SEQ ID NO:3 or SEQ ID NO:4 or both.

The present invention also relates to an isolated polypeptide having an amino acid sequence corresponding to SEQ ID NO:10.

The present invention also relates to an antigenic polypeptide comprising a portion, but not all, of an amino acid sequence corresponding to SEQ ID NO:10.

The present invention also relates to a method for inhibiting the formation of IKKγΔ-containing IKK in a sample. The method includes contacting the sample with a compound which inhibits the expression or function of IKKγΔ.

The present invention also relates to a method for inhibiting NF-κB activation in a sample. The method includes contacting the sample with a compound which inhibits the expression or function of IKKγΔ.

The present invention also relates to a method for treating or preventing inflammation in a subject. The method includes administering, to the subject, a compound which inhibits the expression or function of IKKγΔ.

The present invention also relates to a RNA oligomer capable of hybridizing to a nucleic acid molecule encoding a polypeptide having an amino acid sequence corresponding to SEQ ID NO:10.

BRIEF DESCRIPTION OF THE DRAWINGS

FIG. 1 is a nucleic acid sequence (SEQ ID NO: 2) and amino acid sequence (SEQ ID NO: 1) of IKKγΔ.

FIG. 2 is a nucleic acid sequence (SEQ ID NO: 9) and amino acid sequence (SEQ ID NO: 8) of IKKγ.

FIG. 3 is a pair of nucleic acid sequences showing the alignment of portions of wild type IKKγ (SEQ. ID. NO:11) with alternatively spliced IKKγΔ (SEQ. ID. NO:12).

FIG. 4 is an image of a Western immunoblot of epitope-tagged IKKγ proteins.

FIG. 5 is an image of an IP-kinase assay which compares the functional activities of wild type IKKγ and IKKγΔ.

FIG. 6 is an image of a Western blot of an RT-PCR assay for identifying the expression of wild type IKKγ and IKKγΔ in epithelial cells.

DETAILED DESCRIPTION OF THE INVENTION

Figure 7:
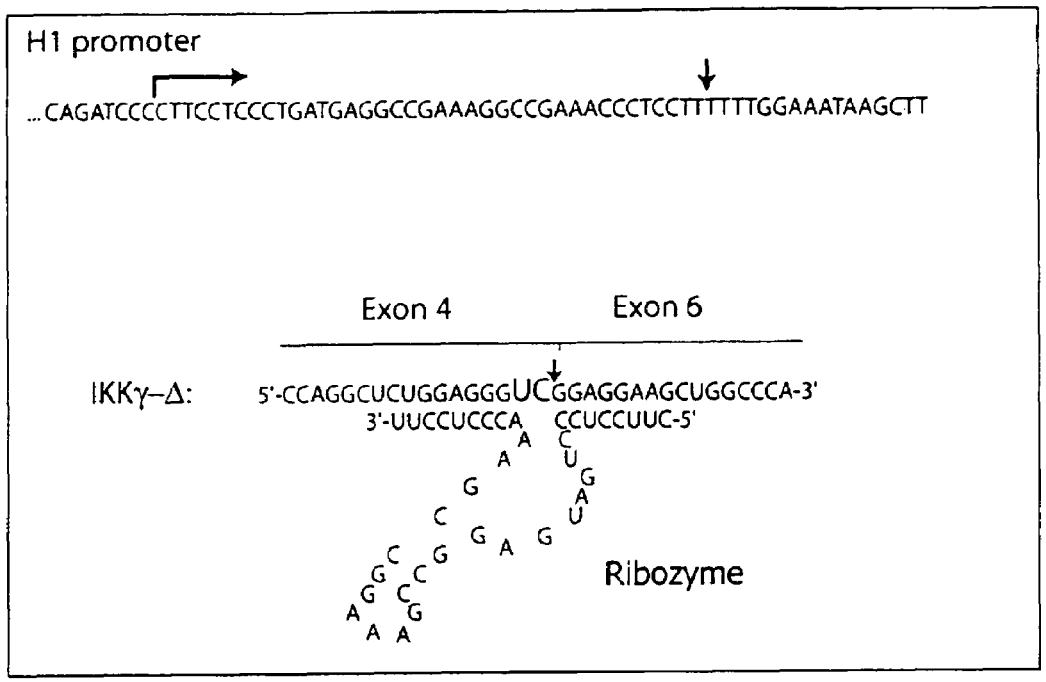
FIG. 7 is a schematic diagram of pH1-R2 expression plasmid.

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA, and nonfunctional DNA or RNA.

"Isolated" nucleic acid refers to nucleic acid which has been separated from an organism and to synthetic nucleic acid. The isolated nucleic acid can be in purified form (e.g., substantially free of other substances originating from an organism).

By a nucleic acid sequence "homologous to" or "complementary to", it is meant a nucleic acid that selectively hybridizes, duplexes, or binds to DNA sequences encoding the protein or portions thereof when the DNA sequences encoding the protein are present in a genomic or cDNA library. A DNA sequence which is similar or complementary to a target sequence can include sequences which are shorter or longer than the target sequence so long as they meet the functional test set forth.

Typically, the hybridization is done in a Southern blot protocol using a 0.2×SSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein or peptide. The nucleic acid molecule includes both the full length nucleic acid sequences as well as non-full length sequences derived from the full length protein. It being further understood that the sequence includes the degenerate codons of the native sequence or sequences which may be introduced to provide codon preference in a specific host cell.

The term "vector", refers to viral expression systems, autonomous self-replicating circular DNA (plasmids), and includes both expression and nonexpression plasmids. Where a recombinant microorganism or cell is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or the vector may be incorporated within the host's genome.

The term "plasmid" refers to an autonomous circular DNA molecule capable of replication in a cell, and includes both the expression and nonexpression types. Where a recombinant microorganism or cell is described as hosting an "expression plasmid", this includes latent viral DNA integrated into the host chromosome(s). Where a plasmid is being maintained by a host cell, the plasmid is either being stably replicated by the cell during mitosis as an autonomous structure, or the plasmid is incorporated within the host's genome.

The phrase "heterologous protein" or "recombinantly produced heterologous protein" refers to a peptide or protein of interest produced using cells that do not have an endogenous copy of DNA able to express the peptide or protein of interest. The cells produce the peptide or protein because they have been genetically altered by the introduction of the appropriate nucleic acid sequences. The recombinant peptide or protein will not be found in association with peptides or proteins and other subcellular components normally associated with the cells producing the peptide or protein.

The following terms are used to describe the sequence relationships between two or more nucleic acid molecules or polynucleotides, or between two or more amino acid sequences of peptides or proteins: "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted, for example, by the local homology algorithm of Smith and Waterman, Adv Appl Math 2:482 (1981); by the homology alignment algorithm of Needleman and Wunsch, J Mol Biol 48:443 (1970); by the search for similarity method of Pearson and Lipman, Proc Natl Acad Sci USA 85:2444; or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to nucleic acid molecules or polynucleotides, the terms "substantial identity" or "substantial sequence identity" mean that two nucleic acid sequences, when optimally aligned (see above), share at least 90 percent sequence identity, preferably at least 95 percent sequence identity, more preferably at least 96, 97, 98 or 99 percent sequence identity.

"Percentage nucleotide (or nucleic acid) identity" or "percentage nucleotide (or nucleic acid) sequence identity" refers to a comparison of the nucleotides of two nucleic acid molecules which, when optimally aligned, have approximately the designated percentage of the same nucleotides. For example, "95% nucleotide identity" refers to a comparison of the nucleotides of two nucleic acid molecules which when optimally aligned have 95% nucleotide identity. Preferably, nucleotide positions which are not identical differ by redundant nucleotide substitutions (the nucleotide substitution does not change the amino acid encoded by the particular codon).

As further applied to nucleic acid molecules or polynucleotides, the terms "substantial homology" or "substantial sequence homology" mean that two nucleic acid sequences, when optimally aligned (see above), share at least 90 percent sequence homology, preferably at least 95 percent sequence homology, more preferably at least 96, 97, 98 or 99 percent sequence homology.

"Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides which are not identical but differ by redundant nucleotide substitutions (the nucleotide substitution does not change the amino acid encoded by the particular codon). For example, "95% nucleotide homology" refers to a comparison of the nucleotides of two nucleic acid molecules which when optimally aligned have 95% nucleotide homology.

As applied to polypeptides, the terms "substantial identity" or "substantial sequence identity" mean that two peptide sequences, when optimally aligned, such as by the programs GAP or BESTFIT using default gap, share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

As further applied to polypeptides, the terms "substantial homology" or "substantial sequence homology" mean that two peptide sequences, when optimally aligned, such as by the programs GAP or BESTFIT using default gap, share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two polypeptides which, when optimally aligned, have approximately the designated percentage of the same amino acids or conservatively substituted amino acids. For example, "95% amino acid homology" refers to a comparison of the amino acids of two polypeptides which when optimally aligned have 95% amino acid homology. As used herein, homology refers to identical amino acids or residue positions which are not identical but differ only by conservative amino acid substitutions. For example, the substitution of amino acids having similar chemical properties such as charge or polarity are not likely to affect the properties of a protein. Examples include glutamine for asparagine or glutamic acid for aspartic acid.

The phrase "isolated" when referring to a protein (or peptide), means a chemical composition which is not contained in an organism or an organism's cell in which it is naturally found. The isolated protein or polypeptide can be "purified", i.e., substantially free from other cellular components. Preferably, the protein or peptide is in a homogeneous state, which is meant to include homogeneous dry (e.g., lyophilized) proteins or homogeneous proteins in aqueous solution. Purity and homogeneity are typically determined using analytical chemistry techniques such as polyacrylamide gel electrophoresis or high performance liquid chromatography. A protein (or peptide) which is the predominant species present in a preparation is, for the purposes of the present invention, to be considered substantially purified. Generally, a purified, isolated protein (or peptide) will comprise more than 80% of all macromolecular species present in the preparation. Preferably, the protein (or peptide) is purified to represent greater than 90% of all macromolecular species present. More preferably the protein (or peptide) is purified to greater than 95%, and most preferably the protein (or peptide) is purified to essential homogeneity, wherein other macromolecular species are not detected by conventional techniques. "Purified" and "isolated" proteins (or peptides) can be synthetically or chemically produced, or they can be recombinantly produced.

"Biological sample" or "sample" as used herein refers to any sample obtained from a living organism or from an organism that has died. Examples of biological samples include body fluids and tissue specimens.

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. High stringency may be attained, for example, by overnight hybridization at about 68° C. in a 6×SSC solution, washing at room temperature with 6×SSC solution, followed by washing at about 68° C. in a 6×SSC solution then in a 0.6×SSX solution.

Hybridization with moderate stringency may be attained, for example, by: 1) filter pre-hybridizing and hybridizing with a solution of 3× sodium chloride, sodium citrate (SSC), 50% formamide, 0.1M Tris buffer at pH 7.5, 5×Denhardt's solution; 2) pre-hybridization at 37° C. for 4 hours; 3) hybridization at 37° C. with amount of labeled probe equal to 3,000,000 cpm total for 16 hours; 4) wash in 2×SSC and 0.1% SDS solution; 5) wash 4× for 1 minute each at room temperature and 4× at 60° C. for 30 minutes each; and 6) dry and expose to film.

The phrase "selectively hybridizing to" refers to a nucleic acid molecule that hybridizes, duplexes, or binds only to a particular target DNA or RNA sequence when the target sequences are present in a preparation of total cellular DNA or RNA. By selectively hybridizing it is meant that a nucleic acid molecule binds to a given target in a manner that is detectable in a different manner from non-target sequence under moderate, or more preferably under high, stringency conditions of hybridization. "Complementary" or "target" nucleic acid sequences refer to those nucleic acid sequences which selectively hybridize to a nucleic acid molecule. Proper annealing conditions depend, for example, upon a nucleic acid molecule's length, base composition, and the number of mismatches and their position on the molecule, and must often be determined empirically. For discussions of nucleic acid molecule (probe) design and annealing conditions, see, for example, Sambrook et al., *Molecular Cloning: A Laboratory Manual,* 2d Edition, Cold Spring Harbor Laboratory Press, Cold Spring Harbor, N.Y. (1989) ("Sambrook").

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the peptide/protein to which the relevant sequence listing relates.

The DNA molecules of the subject invention also include DNA molecules coding for protein analogs, fragments or derivatives of the protein which differ from naturally-occurring forms (the naturally-occurring protein) in terms of the identity or location of one or more amino acid residues (deletion analogs containing less than all of the residues specified for the protein, substitution analogs wherein one or more residues specified are replaced by other residues, and addition analogs wherein one or more amino acid residues are added to a terminal or medial portion of the protein) and which share the function of the naturally-occurring form. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The polypeptides of the present invention can contain naturally-occurring or non-naturally-occurring amino acids, including the D-form of the amino acids, amino acid derivatives, and amino acid mimics. The choice of including an (L)- or a (D)-amino acid in the polypeptides depends, in part, on the desired characteristics of the polypeptide. For example, the incorporation of one or more (D)-amino acids can confer increased stability on the polypeptide and can allow a polypeptide to remain active in the body for an extended period of time. The incorporation of one or more (D)-amino acids can also increase or decrease the pharmacological activity of the polypeptide.

The polypeptides of the present invention may also be cyclized, since cyclization may provide the polypeptides with superior properties over their linear counterparts.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the polypeptide backbone and polypeptide bonds thereof are also encompassed within the scope of amino acid mimic or mimetic. Such modifications can be made to the amino acid, derivative thereof, non-amino acid moiety or the polypeptide either before or after the amino acid, derivative thereof or non-amino acid moiety is incorporated into the polypeptide. What is critical is that such modifications mimic the polypeptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC, 46:257 (1981) and Raucher et al., Tetrahedron. Lett., 21:14061 (1980). An amino acid mimic is, therefore, an organic molecule that retains the similar amino acid pharmacophore groups as is present in the corresponding amino acid and which exhibits substantially the same spatial arrangement between functional groups.

The substitution of amino acids by non-naturally occurring amino acids and amino acid mimics as described above can enhance the overall activity or properties of an individual polypeptide based on the modifications to the backbone or side chain functionalities. For example, these types of alterations to the amino acid substituents and polypeptides can enhance the polypeptide's stability to enzymatic breakdown and increase biological activity. Modifications to the polypeptide backbone similarly can add stability and enhance activity.

One skilled in the art, using the sequences or formulae described herein, can easily synthesize the polypeptides of the present invention. Standard procedures for preparing synthetic polypeptides are well known in the art. For example, the novel polypeptides can be synthesized using: the solid phase peptide synthesis (SPPS) method of Merrifield (J. Am. Chem. Soc., 85:2149 (1964)) or modifications of SPPS; or, the peptides can be synthesized using standard solution methods well known in the art (see, for example, Bodanzsky, M., Principles of Peptide Synthesis, 2nd revised ed., Springer-Verlag (1988 and 1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82:5131 (1985).

As used herein, SEQ ID NO:1 refers to the amino acid sequence set forth in FIG. 1. As used herein, SEQ ID NO:2 refers to the nucleotide sequence set forth in FIG. 1. As used herein, SEQ ID NO:3 is GRR; SEQ ID NO:4 is RRK; SEQ ID NO:5 is GRRK; SEQ ID NO:6 is EGRRKL; and SEQ ID NO:7 is LEGRRKLA. As used herein, SEQ ID NO:8 refers to the amino acid sequence set forth in FIG. 2. As used herein, SEQ ID NO:9 refers to the nucleotide sequence set forth in FIG. 2. As used herein, SEQ ID NO:10 refers to the amino acid sequence set forth below:

A R A A S E Q A R Q L E S E R E A L

Q Q Q H S V Q V D Q L R M Q G Q S V E A

A L R M E R Q A A S E E K

With these definitions in mind, the subject invention relates, in part, to isolated IKKγΔ; isolated nucleic acid molecules encoding IKKγΔ; expression vectors and cells which contain such nucleic acid molecules; oligonucleotides which are complementary to at least a portion of nucleic acid molecules encoding IKKγΔ but which are not complementary to any portion of nucleic acid molecules encoding wild type IKKγ; antibodies which are specific for IKKγΔ; DNA and RNA oligomers, optionally in labeled or enzymatically active form, which are capable of selectively hybridizing to nucleic acid molecules encoding IKKγΔ; and DNA and RNA oligomers, optionally in labeled or enzymatically active form, which are capable of selectively hybridizing to nucleic acid molecules encoding IKKγΔ but which do not hybridize with nucleic acid molecules encoding wild type IKKγ.

More particularly, the subject invention relates to an isolated polypeptide having an amino acid sequence corresponding to SEQ ID NO:1. As used herein, "a polypeptide having an amino acid sequence of" a specified sequence is meant to include only the polypeptide having the exact specified sequence. As used herein, "a polypeptide having an amino acid sequence corresponding to" a specified sequence is meant to include the polypeptide having the exact specified sequence as well as those polypeptides having substantial identity with the specified sequence and those polypeptides having substantial homology with the specified sequence.

The subject invention also relates to an isolated polypeptide having an amino acid sequence corresponding to an antigenic portion of SEQ ID NO:1, wherein the isolated polypeptide comprises an amino acid sequence corresponding to either SEQ ID NO:3 or SEQ ID NO:4 or both. Such polypeptides include those which comprise an amino acid sequence corresponding to any one or more of SEQ ID NO:5, SEQ ID NO:6, and/or SEQ ID NO:7.

The polypeptides of the present invention can be purified or not purified, and they can be produced by any suitable method, such as recombinantly or synthetically.

The present invention also relates to an isolated nucleic acid molecule encoding a polypeptide of the present invention. Illustratively, the present invention also relates to an isolated nucleic acid molecule having an amino acid sequence corresponding to SEQ ID NO:1. A nucleic acid molecule having SEQ ID NO:2 is one example of a suitable nucleic acid molecule encoding an amino acid sequence corresponding to SEQ ID NO:1. As used herein, "a nucleic acid molecule having an nucleic acid sequence of" a specified sequence is meant to include only the nucleic acid molecule having the exact specified sequence. As used herein, "a nucleic acid molecule having an nucleic acid sequence corresponding to" a specified sequence is meant to include the nucleic acid molecule having the exact specified sequence as well as those nucleic acid molecules having substantial identity with the specified sequence and those nucleic acid molecules having substantial homology with the specified sequence.

The nucleic acid molecule can be deoxyribonucleic acid ("DNA") or ribonucleic acid ("RNA"). RNA, as used herein, is meant to include messenger RNA ("mRNA"). The nucleic acid molecule can be genomic or recombinant, biologically isolated or synthetic, purified or not purified.

The DNA molecule can be a cDNA molecule, which is a DNA copy of an mRNA encoding subject polypeptides.

The polypeptides of the present invention can be produced recombinantly, for example, by introducing the nucleic acid molecules of the subject invention in a suitable host cell and causing the host cell to express the polypeptides using conventional techniques. Any suitable host and/or vector system can be used.

Techniques for introducing the nucleic acid molecules into the host cells can involve the use of expression vectors which comprise the nucleic acid molecules of the present invention (e.g., nucleic acid molecules having a nucleotide sequence corresponding to SEQ ID NO:2 and other nucleic acid molecules encoding an amino acid sequence corresponding to SEQ ID NO:1). These expression vectors (such as plasmids and viruses; viruses being meant to include bacteriophages) can then be used to introduce the nucleic acid molecules into suitable host cells. For example, DNA molecules of the present invention can be injected into the nucleus of a host cell or transformed into the host cell using a suitable vector, or mRNA molecules of the present invention (e.g., nucleic acid molecules corresponding to SEQ ID NO:2) can be injected directly into the host cell, in order to obtain expression of the polypeptides of the present invention in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino, R. J. and Gould-Fogerite, S., BioTechniques 6:682-690 (1988); Shigekawa, K. and Dower, W. J., BioTechniques 6:742-751 (1988); Capecchi, M., Cell 22:479-488 (1980); and Klein, T. M., et al., Nature 327:70-73 (1987).

Further methods for introducing nucleic acid molecules into cells involve the use of viral vectors. One such virus widely used for protein production is an insect virus, baculovirus. For a review of baculovirus vectors, see Miller, L. K., Bioessays 11:91-95 (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook.

Host cells into which the nucleic acids of the present invention have been introduced can be used to produce the polypeptides of the present invention.

Various modifications of the nucleic acid and amino acid sequences disclosed herein are covered by the subject invention. The invention, for example, further provides an isolated nucleic acid molecule which encodes a first amino acid sequence having at least 90% amino acid identity to a second amino acid sequence, the second amino acid sequence being that of a polypeptide having an amino acid sequence of SEQ ID NO:1. In further embodiments, the first amino acid sequence has at least 95%, 96%, 97%, 98%, or 99% amino acid identity to SEQ ID NO:1.

The invention further provides an isolated DNA or RNA oligomer capable of selectively hybridizing to the nucleic acid molecule encoding a polypeptide of the present invention. Illustratively, the present invention relates to a DNA oligomer capable of selectively hybridizing to a nucleic acid molecule encoding a polypeptide having an amino acid sequence corresponding to SEQ ID NO:1. As further illustration, the present invention relates to a DNA oligomer capable of selectively hybridizing to a nucleic acid molecule encoding a polypeptide having an amino acid sequence corresponding to SEQ ID NO:1, wherein the DNA oligomer does not hybridize to a nucleic acid molecule encoding a polypeptide having an amino acid sequence corresponding to SEQ ID NO:8. As still further illustration, the present invention relates to a DNA oligomer capable of selectively hybridizing to a nucleic acid molecule encoding a polypeptide having an amino acid sequence corresponding to SEQ ID NO:1, wherein the DNA oligomer does not hybridize to SEQ ID NO:9. As yet further illustration, the present invention relates to a DNA oligomer which is capable of selectively hybridizing to a nucleic acid molecule encoding a polypeptide having an amino acid sequence corresponding to SEQ ID NO:1, wherein the DNA oligomer comprises a nucleotide sequence encoding either SEQ ID NO:3 or SEQ ID NO:4 or both. As yet further illustration, the present invention relates to a DNA oligomer which is capable of selectively hybridizing to a nucleic acid molecule encoding a polypeptide having an amino acid sequence corresponding to SEQ ID NO:1, wherein the DNA oligomer comprises a nucleotide sequence encoding any one or more of SEQ ID NO:5, SEQ ID NO:6, and/or SEQ ID NO:7. Still illustratively, the present invention relates to an RNA oligomer capable of selectively hybridizing to a nucleic acid molecule encoding a polypeptide having an amino acid sequence corresponding to SEQ ID NO:1. As further illustration, the present invention relates to an RNA oligomer capable of selectively hybridizing to a nucleic acid molecule encoding a polypeptide having an amino acid sequence corresponding to SEQ ID NO:1, wherein the RNA oligomer does not hybridize to a nucleic acid molecule encoding a polypeptide having an amino acid sequence corresponding to SEQ ID NO:8. As still further illustration, the present invention relates to an RNA oligomer capable of selectively hybridizing to a nucleic acid molecule encoding a polypeptide having an amino acid sequence corresponding to SEQ ID NO:1, wherein the RNA oligomer does not hybridize to SEQ ID NO:9. As yet further illustration, the present invention relates to an RNA oligomer which is capable of selectively hybridizing to a nucleic acid molecule encoding a polypeptide having an amino acid sequence corresponding to SEQ ID NO:1, wherein the RNA oligomer comprises a nucleotide sequence encoding either SEQ ID NO:3 or SEQ ID NO:4 or both. As yet further illustration, the present invention relates to an RNA oligomer which is capable of selectively hybridizing to a nucleic acid molecule encoding a polypeptide having an amino acid sequence corresponding to SEQ ID NO:1, wherein the RNA oligomer comprises a nucleotide sequence encoding any one or more of SEQ ID NO:5, SEQ ID NO:6, and/or SEQ ID NO:7.

The aforementioned DNA or RNA oligomer capable of selectively hybridizing to the nucleic acid molecule encoding a polypeptide of the present invention can be used as probes in a method of detecting the presence of the splice variant mRNA in a sample. More particularly, a sample can be contacted with one of the aforementioned oligomers under conditions effective to permit the oligomer to hybridize to splice variant mRNA present in the sample, forming a complex therewith. The complex can then be detected, thereby detecting presence of splice variant mRNA in the sample.

The complex can be detected using methods known in the art. Illustratively, the DNA oligomer can be labeled with a detectable marker so that detection of the marker after the DNA oligomer hybridizes to splice variant mRNA in the sample (wherein non-hybridized DNA oligomer has been removed from the sample, e.g., by washing) permits detection of the complex. Detection of the complex indicates the presence of splice variant mRNA in the sample. As will be readily apparent to those skilled in the art, such a method could also be used quantitatively to assess the amount of splice variant mRNA in a sample.

For detection, the oligomers can be labeled with, for example, a radioactive isotope, biotin, an element opaque to X-rays, or a paramagnetic ion. Radioactive isotopes are commonly used and are well known to those skilled in the art. Representative examples include indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, X-ray, CAT scan, PET scan, NMRI, and fluoroscopy. Other suitable labels include enzymatic labels (horseradish peroxidase, alkaline phosphatase, etc.) and fluorescent labels (such as FITC or rhodamine, etc.).

The aforementioned DNA or RNA oligomer capable of selectively hybridizing to a nucleic acid molecule encoding a polypeptide of the present invention can be present alone, for example, as in the case where the DNA or RNA oligomer is used as a starting material to which a label is bound, or the DNA or RNA oligomer can further comprise other moieties. Illustratively, the DNA or RNA oligomer can further comprise a labeling moiety, such as those discussed above, and the present invention thus relates to the above-described DNA or RNA oligomers in detectably labeled form. Further illustratively, the DNA or RNA oligomer can further comprise an enzymatic moiety, such as those discussed below, and the present invention thus relates to the above-described DNA or RNA oligomers in an enzymatically active form.

Enzymatically active DNA or RNA oligomers of the present invention (sometimes referred to herein as "enzymatic nucleic acid molecules") include DNA or RNA oligomers capable of selectively hybridizing to a target nucleic acid molecule encoding a polypeptide of the present invention and possessing enzymatic activity, such as enzymatic activity capable interfering with transcription or translation of the targeted nucleic acid molecule. Such enzymatically active DNA or RNA oligomers of the present invention are meant to include ribozymes, catalytic RNAs, enzymatic RNAs, catalytic DNAs, aptazymes or aptamer-binding ribozymes, regulatable ribozymes, catalytic oligonucleotides, nucleozymes, DNAzymes, RNA enzymes, endoribonucleases, endonucleases, minizymes, leadzymes, oligozymes, and/or DNA enzymes, as well as other nucleic acid molecules having cleaving, ligation, and/or other enzymatic activity. For example, the present invention is directed to a ribozyme which comprises an RNA oligomer (i) which is capable of selectively hybridizing to a nucleic acid molecule encoding a polypeptide having an amino acid sequence corresponding to SEQ ID NO:1; (ii) which is capable of selectively hybridizing to a nucleic acid molecule encoding a polypeptide having an amino acid sequence corresponding to SEQ ID NO:1, wherein the RNA oligomer does not hybridize to a nucleic acid molecule encoding a polypeptide having an amino acid sequence corresponding to SEQ ID NO:8; (iii) which is capable of selectively hybridizing to a nucleic acid molecule encoding a polypeptide having an amino acid sequence corresponding to SEQ ID NO:1, wherein the RNA oligomer does not hybridize to SEQ ID NO:9; (iv) which is capable of selectively hybridizing to a nucleic acid molecule encoding a polypeptide having an amino acid sequence corresponding to SEQ ID NO:1, wherein the RNA oligomer comprises a nucleotide sequence encoding either SEQ ID NO:3 or SEQ ID NO:4 or both; and/or (v) which is capable of selectively hybridizing to a nucleic acid molecule encoding a polypeptide having an amino acid sequence corresponding to SEQ ID NO:1, wherein the RNA oligomer comprises a nucleotide sequence encoding any one or more of SEQ ID NO:5, SEQ ID NO:6, and/or SEQ ID NO:7. The ribozymes and other enzymatically active DNA or RNA oligomers of the present invention can be prepared and optimized using conventional methodologies, such as those described in U.S. Patent Application Publication No. US-2003-0119017 of McSwiggen.

As indicated above, the present invention relates to an isolated polypeptide having an amino acid sequence corresponding to SEQ ID NO:1. The present invention also relates to amino acid sequences having at least 90% amino acid identity to a second amino acid sequence, the second amino acid sequence being as shown in SEQ ID NO:1. In further embodiments, the first amino acid sequence has at least 95%, 96%, 97%, 98%, or 99% amino acid identity to SEQ ID NO:1.

The polypeptides described above can be used in a variety of ways. Illustratively, they can be used to prepare antibodies which specifically recognize IKKγΔ, as described further below.

The invention further relates to an antibody or fragment thereof specific for polypeptides of the present invention. Antibodies of the subject invention include polyclonal antibodies and monoclonal antibodies capable of binding to the polypeptides of the present invention, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the F(ab')$_2$, and the Fc fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell, A. M., *Monoclonal Antibody Technology: Laboratory Techniques in Biochemistry and Molecular Biology*, Elsevier Science Publishers, Amsterdam, The Netherlands (1984) and St. Groth, et al., J Immunol Methods 35:1-21 (1980) ("Campbell")). Any animal (mouse, rabbit, etc.) which is known to produce antibodies can be immunized with the antigenic polypeptides of the present invention (or an antigenic fragment thereof). Methods for immunization are well known in the art. Such methods include subcutaneous or intraperitoneal injection of the polypeptide. One skilled in the art will recognize that the amount of the polypeptide used for immunization will vary based on the animal which is immunized, the antigenicity of the polypeptide, and the site of injection.

The polypeptide which is used as an immunogen may be modified or administered in an adjuvant in order to increase the polypeptide's antigenicity. Methods of increasing the antigenicity of a polypeptide are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz, et al., Exp Cell Res 175:109-124 (1988)).

Hybridomas secreting the desired antibodies are cloned and the class and subclass are determined using procedures known in the art (see, e.g., Campbell).

For polyclonal antibodies, antibody containing antisera is isolated from the immunized animal and is screened for the presence of antibodies with the desired specificity using one of the above-described procedures.

In accordance with the above discussion, the subject invention further provides a method of producing an antibody specific for a polypeptide of the present invention in a host. The method comprises selecting the isolated polypeptide of the present invention or an antigenic portion thereof and introducing the selected polypeptide of the present invention or antigenic portion thereof into a host to induce production of an antibody specific for polypeptide of the present invention in the host.

The present invention also relates to the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art (for example see Sternberger, L. A., et al., J Histochem Cytochem 18:315 (1970); Bayer, E. A., et al., Meth Enzym 62:308 (1979); Engval, E., et al., Immunol 109:129 (1972); and Goding, J. W., J Immunol Meth 13:215 (1976)).

The labeled antibodies or fragments thereof of the present invention can be used for in vitro, in vivo, and in situ assays to identify cells or tissues which express the polypeptides of the present invention, to identify samples containing polypeptides of the present invention, or to detect the presence of polypeptides of the present invention in a sample. More particularly, the antibodies or fragments thereof can thus be used to detect the presence of polypeptides of the present invention in a sample, by contacting the sample with the antibody or fragment thereof. The antibody or fragment thereof binds to polypeptides of the present invention present in the sample, forming a complex therewith. The complex can then be detected, thereby detecting the presence of polypeptides of the present invention in the sample. As will be readily apparent to those skilled in the art, such a method could also be used quantitatively to assess the amount of polypeptide of the present invention in a sample.

The present invention, in another aspect thereof, relates to methods for inhibiting the formation of IKKγΔ-containing IKK in a sample. The method includes contacting the sample with a compound which inhibits the expression or function of IKKγΔ. The mechanism by which the compound inhibits the expression or function of IKKγΔ is not particularly critical. Illustratively, IKKγΔ expression can be inhibited by interfering with the transcription process and/or the translation process by which IKKγΔ is produced. Alternatively, IKKγΔ function can be inhibited by interfering with the ability of IKKγΔ to form IKK complex.

In accordance with the method of the present invention, formation of IKKγΔ-containing IKK in a sample is inhibited by contacting the sample with a compound which inhibits the expression or function of IKKγΔ.

Examples of compounds which inhibit the expression of IKKγΔ include, for example, the above-described DNA or RNA oligomers of the present invention, such as the above-described ribozymes or other enzymatically active DNA or RNA oligomers of the present invention. Such compounds which inhibit the expression of IKKγΔ can be selected so as to inhibit the expression of IKKγΔ to a degree greater than the degree to which they inhibit the expression of wild-type IKKγ, for example, as in the case where the compound inhibits the expression of IKKγΔ but fails to substantially inhibit the expression of wild-type IKKγ. While it is preferred that the compound be selected so as to substantially inhibit the expression of IKKγΔ, such need not be the case. As used in this context, a compound is to be deemed to substantially inhibit the expression of X if the amount of X produced in the presence of the compound is less than about 70% (e.g., less than about 60%, less than about 50%, less than about 40%, less than about 30%, less than about 20%, and/or less than about 10%) of the amount of X produced in the absence of the compound or if the amount of X produced in the presence of the compound is immeasurably small.

Examples of compounds which inhibit the function of IKKγΔ include, for example, the above-described antibodies of the present invention. Such antibodies can be selected so as to inhibit the function of IKKγΔ to a degree greater than the degree to which they inhibit the function of wild-type IKKγ, for example, as in the case where the compound inhibits the function of IKKγΔ but fails to substantially inhibit the function of wild-type IKKγ. While it is preferred that the compound be selected so as to substantially inhibit the function of IKKγΔ, such need not be the case. As used in this context, a compound is to be deemed to substantially inhibit the function of X if the amount of X incorporated into IKK in the presence of the compound is less than about 70% (e.g., less than about 60%, less than about 50%, less than about 40%, less than about 30%, less than about 20%, and/or less than about 10%) of the amount of X incorporated into IKK in the absence of the compound or if the amount of X incorporated into IKK in the presence of the compound is immeasurably small.

The above-described methods for inhibiting the formation of IKKγΔ-containing IKK in a sample can be carried out in vivo (as in the case where the sample is a patient, such as a mouse, rat, dog, cat, rabbit, human, or other mammal, or a tissue, cell, or other portion thereof), or the methods can be carried out in vitro. In cases where the method is carried out in a patient, contact can be made by any suitable means, such as by administering the compound systemically to the patient or by introducing the compound to a specific tissue, cell, or other portion of the patient.

The present invention, in another aspect thereof, relates to methods for inhibiting NF-κB activation in a sample. The method includes contacting the sample with a compound which inhibits the expression or function of IKKγΔ. Again, the mechanism by which the compound inhibits the expression or function of IKKγΔ is not particularly critical. Illustratively, IKKγΔ expression can be inhibited by interfering with the transcription process and/or the translation process by which IKKγΔ is produced. Alternatively, IKKγΔ function can be inhibited by interfering with the ability of IKKγΔ to form IKK complex.

In accordance with the method of the present invention, NF-κB activation in a sample is inhibited by contacting the sample with a compound which inhibits the expression or function of IKKγΔ.

Examples of compounds which inhibit the expression of IKKγΔ include, for example, the above-described DNA or RNA oligomers of the present invention, such as the above-described ribozymes or other enzymatically active DNA or RNA oligomers of the present invention. Such compounds which inhibit the expression of IKKγΔ can be selected so as to inhibit the expression of IKKγΔ to a degree greater than the degree to which they inhibit the expression of wild-type IKKγ, for example, as in the case where the compound inhibits the expression of IKKγΔ but fails to substantially inhibit the expression of wild-type IKKγ. While it is preferred that the compound be selected so as to substantially inhibit the expression of IKKγΔ, such need not be the case. As used in this context, a compound is to be deemed to substantially inhibit the expression of X if the amount of X produced in the presence of the compound is less than about 70% (e.g., less than about 60%, less than about 50%, less than about 40%, less than about 30%, less than about 20%, and/or less than about 10%) of the amount of X produced in the absence of the compound or if the amount of X produced in the presence of the compound is immeasurably small.

Examples of compounds which inhibit the function of IKKγΔ include, for example, the above-described antibodies of the present invention. Such antibodies can be selected so as to inhibit the function of IKKγΔ to a degree greater than the degree to which they inhibit the function of wild-type IKKγ, for example, as in the case where the compound inhibits the function of IKKγΔ but fails to substantially inhibit the function of wild-type IKKγ. While it is preferred that the compound be selected so as to substantially inhibit the function of IKKγΔ, such need not be the case. As used in this context, a compound is to be deemed to substantially inhibit the function of X if the amount of X incorporated into IKK in the presence of the compound is less than about 70% (e.g., less than about 60%, less than about 50%, less than about 40%, less than about 30%, less than about 20%, and/or less than about 10%) of the amount of X incorporated into IKK in the absence of the compound or if the amount of X incorporated into IKK in the presence of the compound is immeasurably small.

The above-described methods for inhibiting NF-κB activation in a sample can be carried out in vivo (as in the case where the sample is a patient, such as a mouse, rat, dog, cat, rabbit, human, or other mammal, or a tissue, cell, or other portion thereof), or the methods can be carried out in vitro. In cases where the method is carried out in a patient, contact can be made by any suitable means, such as by administering the compound systemically to the patient or by introducing the compound to a specific tissue, cell, or other portion of the patient.

The present invention, in another aspect thereof, relates to methods for treating or preventing inflammation in a subject. The method includes administering, to the subject, a compound which inhibits the expression or function of IKKγΔ. Again, the mechanism by which the compound inhibits the expression or function of IKKγΔ is not particularly critical. Illustratively, IKKγΔ expression can be inhibited by interfering with the transcription process and/or the translation process by which IKKγΔ is produced. Alternatively, IKKγΔ function can be inhibited by interfering with the ability of IKKγΔ to form IKK complex.

Examples of compounds which inhibit the expression of IKKγΔ include, for example, the above-described DNA or RNA oligomers of the present invention, such as the above-described ribozymes or other enzymatically active DNA or RNA oligomers of the present invention. Such compounds which inhibit the expression of IKKγΔ can be selected so as to inhibit the expression of IKKγΔ to a degree greater than the degree to which they inhibit the expression of wild-type IKKγ, for example, as in the case where the compound inhibits the expression of IKKγΔ but fails to substantially inhibit the expression of wild-type IKKγ. While it is preferred that the compound be selected so as to substantially inhibit the expression of IKKγΔ, such need not be the case. As used in this context, a compound is to be deemed to substantially inhibit the expression of X if the amount of X produced in the presence of the compound is less than about 70% (e.g., less than about 60%, less than about 50%, less than about 40%, less than about 30%, less than about 20%, and/or less than about 10%) of the amount of X produced in the absence of the compound or if the amount of X produced in the presence of the compound is immeasurably small.

Examples of compounds which inhibit the function of IKKγΔ include, for example, the above-described antibodies of the present invention. Such antibodies can be selected so as to inhibit the function of IKKγΔ to a degree greater than the degree to which they inhibit the function of wild-type IKKγ, for example, as in the case where the compound inhibits the function of IKKγΔ but fails to substantially inhibit the function of wild-type IKKγ. While it is preferred that the compound be selected so as to substantially inhibit the function of IKKγΔ, such need not be the case. As used in this context, a compound is to be deemed to substantially inhibit the function of X if the amount of X incorporated into IKK in the presence of the compound is less than about 70% (e.g., less than about 60%, less than about 50%, less than about 40%, less than about 30%, less than about 20%, and/or less than about 10%) of the amount of X incorporated into IKK in the absence of the compound or if the amount of X incorporated into IKK in the presence of the compound is immeasurably small.

The compound which inhibits the expression or function of IKKγΔ can be administered to the subject by any suitable route, either systemically or locally.

Illustratively, the compound can be administered locally to the site or sites where inflammation is to be prevented or treated. For example, where the inflammation is bronchiolitis or asthma or COPD or viral induced airway inflammation or other inflammation of the subject's airway epithelium (e.g., in the subject's bronchial passages), administration can be carried out by administering the ribozyme, oligonucleotide, or other compound as described above to the subject's airway, for example, as an inhaled aerosol or mist delivered via the mouth or via the nose. Where the inflammation is rhinitis or other inflammation of the subject's nasal mucus membranes, administration can be carried out by administering the compound to the subject's nasal cavity, for example, as an inhaled aerosol or mist delivered via the nose or as a topical salve applied to the nasal cavity. Where the inflammation is conjunctivitis or other inflammation of the subject's eye, administration can be carried out by administering the compound to the subject's eye, for example, as a liquid solution or suspension applied, for example, as drops to the eye. Where the inflammation is inflammation of the mucus membranes of the subject's gastrointestinal lumen, administration can be carried out by administering the compound to the subject's gastrointestinal tract, for example, as a liquid solution or suspension, capsule, or tablet. Where the inflammation is atopic dermatitis or other inflammation of the subject's skin, administration can be carried out by topically administering the compound to the subject's skin, for example, as a liquid solution or suspension or as a salve. Where the inflammation is rheumatoid arthritis or other inflammation of the subject's joints, administration can be carried out by injecting the compound into to the subject's joints, for example, as a liquid solution or suspension. Where the inflammation is inflammatory bowel syndrome or other inflammation of the subject's bowel, administration can be carried out orally, for example, as a liquid solution or suspension, capsule, or tablet, or administration can be carried out rectally, for example, in the form of a rectal suppository. Where the inflammation is vascular inflammation (for example, as in the case where the patient suffers from atherosclerosis, suffers from coronary artery disease, and/or is at risk for vascular inflammation following vascular procedures such as angioplasty, administration can be carried out intravenously.

Irrespective of whether the compound is administered for therapeutic or preventative purposes, it will be appreciated that the actual preferred effective amount of compound will vary according to the compound employed, the particular composition formulated, and the mode of administration. Many factors that can modify the compound's activity will be taken into account by those skilled in the art, e.g., species, body weight, sex, diet, time of administration, route of administration, rate of excretion, condition of the subject, and reaction sensitivities and severities.

Illustratively, the compound can be administered in a single daily dose, or in multiple doses, or even continuously. Continuous administration can be carried out, for example, using a slow-release suspension or other slow-release formulation. The compound can be administered by any mode of systemic drug administration, including oral administration or parenteral (e.g. intradermal, intraventricular, intracerebral, intramuscular, intravenous, intraperitoneal, rectal, and subcutaneous) administration, or it can be administered locally.

The compound can be administered alone or in combination with suitable pharmaceutical carriers or diluents. The diluent or carrier ingredients should be selected so that they do not diminish the therapeutic or preventative effects of the compound.

Pharmaceutical and opthalmological formulations of the present invention can be prepared according to conventional formulating techniques. The pharmaceutical and opthalmological formulations can include any suitable pharmacologically acceptable carrier or adjuvant, selected, for example, based on the dosage form of the preparation and the route of administration.

For example, for topical dosage forms to be applied to the eye, eye drop formulations can include buffering agents to ensure that the formulation is isotonic. This typically involves adjusting the acidity or alkalinity of the formulation so that it has the same or similar pH to mammalian eye fluids. pH values of between 6.1 to 6.3 are suitable. Various buffering agents can be employed in this regard, such as one or more of zinc sulfate, boric acid, and potassium bicarbonate. Typically, the total amount of buffering agents present in the composition ranges from 1 to 15% by weight. The eye drop composition can also include a lubricant, such as carboxymethyl cellulose or other cellulose derivatives. When used, the lubricant can be present, for example, in an amount of 0.01 to 5% by weight of the composition. The composition can also include a preservative, such as benzalkonium chloride and/or other quaternary ammonium preservative agents, phenylmercuric salts, sorbic acid, chlorobutanol, disodium edetate, thimerosal, methyl and propyl paraben, benzyl alcohol, and phenyl ethanol. When used, the preservative can be present, for example, in an amount of 0.1 to 5% by weight of the composition. The eye drop formulation typically includes a vehicle, such as deionized water or mixtures of water and water-miscible solvents (e.g., lower alkanols or arylalkanols), phosphate buffer vehicle systems, isotonic vehicles such as boric acid, sodium chloride, sodium citrate, sodium acetate, and the like, vegetable oils, polyalkylene glycols, and petroleum based jelly, as well as aqueous solutions containing ethyl cellulose, carboxymethyl cellulose and derivatives thereof, hydroxypropylmethyl cellulose, hydroxyethyl cellulose, carbopol, polyvinyl alcohol, polyvinyl pyrrolidone, isopropyl myristate, and other conventionally-employed non-toxic, pharmaceutically acceptable organic and inorganic carriers. The eye drop formulation may also contain non-toxic auxiliary substances such as emulsifying agents, wetting agents, bodying agents, and the like, such as, for example, polyethylene glycols, carbowaxes, and polysorbate 80. Other conventional ingredients can be employed, such as sorbitan monolaurate, triethanolamine, oleate, polyoxyethylene sorbitan 35 monopalmitylate, dioctyl sodium sulfosuccinate, monothioglycerol, thiosorbitol, ethylenediamine tetraacetic acid, and the like. The eye drop formulation can be applied to the eye in any suitable amount, for example, 1 to 8 drops per day. Application of eye drop formulation to the eye can be carried out once a day or in multiple, substantially equal doses (e.g., 2 to 4 times per day).

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Suitable dosage forms for pulmonary delivery to the subject's airways can be in solid or liquid particulate form. Solid or liquid particulate forms of the compound prepared for practicing the present invention include particles of respirable size: that is, particles of a size sufficiently small to pass through the mouth and larynx upon inhalation and into the bronchi and alveoli of the lungs. In general, particles ranging from about 1 to 10 microns in size are within the respirable range. The formulation containing the compound is preferably administered by direct inhalation into the respiratory system for delivery as a mist, or other aerosol, or dry powder. Depending upon the solubility of the particular formulation of compound administered, the daily dose may be divided among one or several unit dose administrations. The doses of the compounds may be provided as one or several prepackaged units. In the manufacture of a dosage form for pulmonary delivery, the compound is typically admixed with, inter alia, an acceptable carrier. The carrier must, of course, be acceptable in the sense of being compatible with any other ingredients in the formulation and must not be deleterious to the patient. The carrier may be a solid, or a liquid, or both and is preferably formulated with the compound as a unit dose formulation. Aerosols of liquid particles comprising the compound may be produced by any suitable means, such as inhalatory delivery systems. One is a traditional nebulizer which works in a mechanism similar to the familiar perfume atomizer. The airborne particles are generated by a jet of air from either a compressor or compressed gas cylinder passing through the device (pressure driven aerosol nebulizer). In addition, other forms utilize an ultrasonic nebulizer by vibrating the liquid at speed of up to about 1 MHz, for example as described in U.S. Pat. No. 4,501,729, which is hereby incorporated by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers contain the compound in a liquid carrier. The carrier is typically sterile water or a dilute aqueous alcoholic solution, which may be isotonic or hypertonic with body fluids. Optional additives include preservatives, such as methyl hydroxybenzoate, flavoring agents, volatile oils, buffering agents, and surfactants which are normally used in the preparation of pharmaceutical compositions. Aerosols of solid particles comprising the compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the compound or of a powder blend which includes the compound, a suitable powder diluent, such as lactose, and an optional surfactant. A second type of illustrative aerosol generator involves us of a metered dose inhaler. Metered dose inhalers are pressurized aerosol dispensers, typically containing a suspension or solution formulation of the compound in a liquified propellant. During use, these devices discharge the formulation through a valve, adapted to deliver a metered volume, e.g., from 10 to 22 microliters to produce a fine particle spray containing the compound. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, and suitable flavoring agents. Any propellant may be used in carrying out the present invention, including both chlorofluorocarbon-containing propellants and non-chlorofluorocarbon-containing propellants. Fluorocarbon aerosol propellants that may be employed in carrying out the present invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3CHFCF_2$, $CF_3CH_2CF_2H$, $CF_3CHFCF_3$, $CF_3CH_2CF_3$, $CF_3CHClCF_2Cl$, $CF_3CHClCF_3$, $CF_3CHClCH_2Cl$, $CF_3CHFCF_2Cl$, and the like. A stabilizer such as a fluoropolymer may optionally be included in formulations of fluorocarbon propellants, such as described in U.S. Pat. No. 5,376,359, which is hereby incorporated by reference. Compositions containing respirable dry particles of micronized compound may be prepared by grinding the dry compound with, e.g., a mortar and pestle or other appropriate grinding device, and then passing the micronized composition through a 400 mesh screen to break up or separate out large agglomerates. The aerosol, whether formed from solid or liquid particles, may be produced by the aerosol generator at a rate of from about 10 to about 150 liters per minute. Aerosols containing greater amounts of compound may be administered more rapidly. Typically, each aerosol may be delivered to the patient for a period from about 30 seconds to about 20 minutes, with a delivery period of about 1 to about 5 minutes being preferred. The particulate composition comprising the compound may optionally contain a carrier which serves to facilitate the formation of an aerosol. A suitable carrier is lactose, which may be blended with the active compound in any suitable ratio. In addition to the compound and carriers and excipients mentioned above, dosage forms for pulmonary delivery may further include other pharmacologically active materials, such as bronchodilators.

Suitable dosage forms for topical application to the skin include salves, creams, lotions, topical sprays, solutions, suspensions, and emulsions. For example, the compound can be formulated in a dermatologically acceptable vehicle compatible with the skin, such as corn oil, aqueous ethanol, isopropanol, sesame oil, propylene glycol, benzyl alcohol, oleyl alcohol, isopropyl esters of fatty acids, such as myristic and palmitic acids, mineral oil, and/or wax. The vehicle can be of such a viscosity and/or wetting power that the composition may be satisfactorily applied to the skin as a continuous film or coating. The amount of compound present in the topical formulation is not particularly critical. Illustratively, the topical formulation can contain from about 0.5 to 10% by weight of the compound. The topical formulation can be applied to the skin once a day, or multiple applications can be used (e.g., 2 to 4 times per day).

Suitable dosage forms for delivery of compound to the nasal cavity can include the compound and a non-toxic pharmaceutically acceptable nasal carrier. Suitable non-toxic pharmaceutically acceptable nasal carriers for use in the methods of the present invention will be apparent to those skilled in the art of nasal pharmaceutical formulations. Obviously the choice of suitable carriers will depend on the exact nature of the particular nasal dosage form desired, as well as on the identity of the compound. For example, the compounds can be formulated into a nasal solution (for use as drops or spray), a nasal suspension, a nasal ointment, or a nasal gel. The nasal solutions, suspensions, and gels can contain, in addition to the compound, a major amount of water (preferably purified water) and minor amounts of other ingredients such as pH adjusters (e.g., a base such as NaOH), emulsifiers or dispersing agents (e.g. polyoxyethylene 20 sorbitan monooleate), buffering agents, preservatives, wetting agents, and gelling agents (e.g. methylcellulose). Also, a sustained release composition (e.g., a sustained release gel) can be readily prepared. The above-mentioned liquid nasal formulations (e.g., solutions or suspensions) can be administered as drops, sprays, or by any other liquid intranasal dosage form. Optionally, the delivery system can be a unit dose delivery system. The volume of solution or suspension delivered per dose can be anywhere from about 5 to 400 microliters, such as from about 50 to about 150 microliters. Delivery systems for these various dosage forms can be dropper bottles, plastic squeeze units, atomizers, and the like, in either unit dose or multiple dose packages.

Dosage forms suitable for parenteral administration include solutions, suspensions, dispersions, emulsions, microcapsules and the like. They may also be manufactured in the form of sterile solid compositions which can be dissolved or suspended in sterile injectable medium immediately before use. They may contain suspending or dispersing agents known in the art. Where microcapsules are employed, they can be readily prepared by conventional microencapsulation techniques, such as those disclosed in, for example, *Encyclopedia of Chemical Technology*, 3rd edition, Volume 15, New York: John Wiley and Sons, pp. 470-493 (1981), which is hereby incorporated by reference.

The present invention, in yet other aspects thereof, relates to DNA and RNA oligomers which are capable of selectively hybridizing to nucleic acid molecules encoding wild type IKKγ but which are not capable of hybridizing to nucleic acid molecules encoding IKKγΔ. Examples of such DNA and RNA oligomers include (i) DNA and RNA oligomers which are capable of selectively hybridizing to a nucleic acid molecule which encode a polypeptide having an amino acid sequence corresponding to SEQ ID NO:8 but which do not hybridize to a nucleic acid molecule having a nucleotide sequence corresponding to SEQ ID NO:2; (ii) DNA and RNA oligomers which are capable of selectively hybridizing to a nucleic acid molecule which encode a polypeptide having an amino acid sequence corresponding to SEQ ID NO:8 but which do not hybridize to a nucleic acid molecule encoding a polypeptide having an amino acid sequence corresponding to SEQ ID NO:1; (iii) DNA and RNA oligomers which are capable of selectively hybridizing to a nucleic acid molecule which encode a polypeptide having an amino acid sequence corresponding to SEQ ID NO:8 but which do not hybridize to a nucleic acid molecule having a nucleotide sequence corresponding to SEQ ID NO:2, wherein at least a portion of the DNA or RNA oligomer hybridizes to at least a portion of a nucleic acid molecule encoding SEQ ID NO:10; and/or (iv) DNA and RNA oligomers which are capable of selectively hybridizing to a nucleic acid molecule which encode a polypeptide having an amino acid sequence corresponding to SEQ ID NO:8 but which do not hybridize to a nucleic acid molecule having a nucleotide sequence corresponding to SEQ ID NO:2, wherein at least a portion of the DNA or RNA oligomer hybridizes to at least a portion of exon 8 of IKKγ.

The aforementioned DNA or RNA oligomers that are capable of selectively hybridizing to nucleic acid molecules encoding wild type IKKγ but that are not capable of hybridizing to nucleic acid molecules encoding IKKγΔ of the present invention can be present alone, for example, as in the case where the DNA or RNA oligomer is used as a starting material to which a label is bound, or the DNA or RNA oligomer can further comprise other moieties. Illustratively, the DNA or RNA oligomer can further comprise a labeling moiety, such as those discussed above, and the present invention thus relates to the above-described DNA or RNA oligomers in detectably labeled form. Further illustratively, the DNA or RNA oligomer can further comprise an enzymatic moiety, such as those discussed above, and the present invention thus relates to the above-described DNA or RNA oligomer in an enzymatically active form, for example, in the form of a ribozyme.

The DNA and RNA oligomers which are capable of selectively hybridizing to nucleic acid molecules encoding wild type IKKγ but which are not capable of hybridizing to nucleic acid molecules encoding IKKγΔ can be used to selectively detect the presence of nucleic acid molecules encoding wild type IKKγ in a sample without obtaining false positives caused by the presence of IKKγΔ in the sample. Labeled DNA and RNA oligomers which are capable of selectively hybridizing to nucleic acid molecules encoding wild type IKKγ but which are not capable of hybridizing to nucleic acid molecules encoding IKKγΔ can also be used, together with differently labeled DNA and RNA oligomers which are capable of selectively hybridizing to nucleic acid molecules encoding wild type IKKγΔ but which are not capable of hybridizing to nucleic acid molecules encoding wild type IKKγ, to quantify the relative amounts of wild type IKKγ-encoding and IKKγΔ encoding nucleic acid molecules in a sample. Moreover, DNA and RNA oligomers which are capable of selectively hybridizing to nucleic acid molecules encoding wild type IKKγ but which are not capable of hybridizing to nucleic acid molecules encoding IKKγΔ in an enzymatically active form can be used to inhibit or otherwise modulate expression of wild type IKKγ without inhibiting or otherwise modulating expression of IKKγΔ.

In yet another aspect thereof, the present invention relates to an isolated polypeptide having an amino acid sequence corresponding to SEQ ID NO:10, as well as to antigenic polypeptides which include a portion, but not all, of an amino acid sequence corresponding to SEQ ID NO:10. Such polypeptides can be purified, as discussed above, and they can be produced synthetically or they can be produced recombinantly. The present invention also provides for nucleic acid molecules (e.g., DNA, cDNA, RNA, mRNA, etc) which encode for such polypeptides of the present invention, as well to as expression vectors (e.g., plasmids and viruses) comprising such nucleic acid molecules and to host cells which contain such expression vectors. The present invention also provides for DNA or RNA oligomers (optionally be in an enzymatically active or labeled form) which are capable of hybridizing to nucleic acid molecules (e.g., DNA, cDNA, RNA, mRNA, etc) which encode for such polypeptides of the present invention. The present invention also provides for antibodies or fragments thereof (e.g., Fab fragments, F(ab')$_2$ fragments, and Fc fragments) that are specific for the above-described polypeptides. Such antibodies can be polyclonal, or they can be monoclonal, and the present invention further relates to hybridomas which produce such monoclonal antibodies. Methods for using such polypeptides having an amino acid sequence corresponding to SEQ ID NO:10, antigenic polypeptides which include a portion, but not all, of an amino acid sequence corresponding to SEQ ID NO:10, and their related nucleic acid molecules, expression vectors, host cells, DNA or RNA oligomers, antibodies, and hybridomas will be apparent in view of the discussion presented above. For example, such polypeptides can be used to produce antibodies or fragments thereof (e.g., Fab fragments, F(ab')$_2$ fragments, and Fc fragments) that detect wild-type IKKγ but not IKKγΔ, and, such antibodies, thus, can be used to selectively detect for the presence of wild-type IKKγ and/or to distinguish between wild-type IKKγ and IKKγΔ in a sample. As further illustration, nucleic acid molecules which encode for such polypeptides of the present invention and related expression vectors and host cells can be used to produce recombinantly the subject polypeptides.

Certain aspects of the present invention are further illustrated with the following examples.

EXAMPLES

Example 1

Cloning of an Alternatively Spliced IKKγ ("IKKγΔ")

We have cloned an alternatively-spliced human IKKγ/NEMO isoform. IKKγ is of special relevance because this is a target for IKK activation through viral proteins, including HTLV-I TAX an adenovirus inhibitor of apoptosis (Morris et al., Proc. Soc. Exp. Biol. Med., 92:544-549 (1956); Murphy et al., Genes & Development, 13:2490-2501 (1999); and Murphy et al., Annu. Rev. Immunol., 12:593-633 (1994)). Briefly, as part of our ongoing studies, we assembled a collection of IKK expression vectors (IKKα, IKKβ, NF-κB inducing kinase, MEKK1), but we were unable to obtain the IKKγ coding sequence. As a result, we performed RT-PCR to amplify the coding sequences(cds) of human IKKγ from oligo dT-primed HeLa cDNA. Under a variety of conditions, two discrete products (1.1 and 1.3 kb) were amplified with about equal intensity. The PCR products were TA-cloned and sequenced in their entirety. The 1.3 kb product exactly encodes the 48 kDa human IKKγ protein, whereas the shorter 1.1 kb sequence encodes a 43 kDa IKKγ protein with a 153 bp in-frame deletion of 51 amino acids in a putative helical region between the first and second leucine zippers. FIG. 3 shows the alignment of IKKγ/NEMO wild type and the alternatively spliced IKKγ/NEMO (IKKγΔ) cDNAs. The complete IKK cds were sequenced and aligned. The IKKγΔ cds exactly matched the longer full length molecule (Jin et al., J. Biomedical Science, 6:115-120 (1998)), but exon 8 was missing in its entirety, producing an inframe deletion of the distal helical domain.

Example 2

IKKγΔ Has Enhanced IKK-Activating Properties

To determine whether there was any functional differences in the IKKγ isoforms, eukaryotic expression vectors encoding epitope-tagged IKKγ and IKKγΔ were constructed in the pcDNAFLAG (pcDNAF-) expression plasmid (Sherman et al., Mol. Endocrinol., 15(3):441-457 (2001)). Cells were transiently transfected with pcDNAF (empty vector), pcDNAF-IKKγ or pcDNAF-IKKγΔ. 48 h later, transient transfectants were isolated and IKKγ presence and abundance were measured by Western immunoblot. FIG. 4 shows the result. More particularly, FIG. 4 is a Western immunoblot of epitope-tagged IKKγ proteins in which two groups of epithelial cells were transiently transfected with empty ("-"), IKKγ WT ("γ WT"), or IKKγΔ ("ΔIKKγ") expression plasmids. One group of cells was acutely stimulated with TNF. A homogeneous population of transient transfectants were isolated and cytoplasmic protein blotted with HRP-conjugated FLAG antibody. IKKγ WT migrates at approximately 48 kDa whereas IKKγΔ is approximately 43 kDa. As seen in FIG. 4, both IKKγ WT and IKKγΔ were expressed at similar abundance.

The functional activities of these equivalently-expressed IKK isoforms were next analyzed by IP-kinase assay. In this assay, in vitro IKK kinase activity associated with equivalent amounts of immunoprecipitated IKKγ or IKKγΔ were compared side by side. We have observed in over 6 independent experiments that IKKγΔ consistently produces higher levels of basal and cytokine-stimulated IKK activity than full length IKKγ. This is shown in FIG. 5. More particularly, epithelial cells were transfected with expression vectors encoding epitope tagged IKKγ. 48 hours later, proteins were isolated and subjected to IKK-kinase assay after immunoprecipitation with anti-FLAG antibodies. Note that the cells transfected with IKKγΔ have higher amounts of IKK activity both in the absence and presence of stimulation. Moreover, note the presence of basal IKK activity is indicative that the IKK is not completely silent in untreated cells, and, in fact, basal IKK activity appears necessary for cell survival). Transient transfection assays confirm these effects on the luciferase reporter activity, where IKKγΔ activates luciferase activity to a greater extent than the unspliced wild type, in the presence of the activating IKKβ kinase.

Example 3

Expression of IKKγΔ in Airway Cells

An RT-PCR assay was developed to identify the expression of spliced and unspliced IKKγ isoforms using primers spanning exon 8. The IKKγ/IKKγΔ expression was confirmed in A549, Hela, Hep2, and HepG2 epithelial cells (not shown). Western blot of A549 cytosolic extracts confirmed the presence of IKKγ and IKKγΔ at approximately similar abundance (FIG. 7). More particularly, expression of wild type IKKγ and IKKγΔ in epithelial cells were studied by preparing cytoplasmic extracts of epithelial cells by high speed ultracentrifugation and detecting the presence of IKKγ isoforms by specific IKKγ antibody (Santa Cruz) that recognizes a shared epitope of both isoforms.

Example 4

Ribozyme-Mediated Depletion of IKKγΔ

Catalytic (hammerhead) ribozymes were used to produce specific transcleavage of target mRNA molecules. Specificity of these agents is achieved by Watson-Crick base pairing on two binding arm sequences flanking a UH cleavage site on the mRNA target that flanks the exon 4-6 boundary of the IKKγΔ mRNA. We modified a eukaryotic expression vector that expressed short, nonpolyadenylated RNA species under control of the polymerase III driven Histone H1 promoter, as shown in FIG. 7. The ribozyme's binding arms recognize exon 4 and 6 and would not therefore cleave wild type IKKγ. In brief, referring to the upper portion of FIG. 7, the Histone H1 promoter was cloned into the pcDNA3 backbone, as described in more detail below. FIG. 7, shows Shown is the sequence flanking the multiple cloning site. The pol III dependent promoter initiates transcription after CCC (indicated by horizontal arrow in the upper portion of FIG. 7), and terminates at 5 thymidines (vertical arrow). The lower portion of FIG. 7 shows hybridization of the hammerhead ribozyme on the exon 4-6 boundary of IKKγΔ. The scissile site is indicated by the vertical arrow after the UH recognition sequence (large font).

More particularly, the Histone H1 promoter expressing the IKKγΔ-specific ribozyme, pH1-R2, was constructed in two steps. The 208 bp polymerase-III dependent Histone H1 promoter was amplified from genomic DNA using the upstream primer 5'-GGATCCAACGCTGACGTC-3' (SEQ ID NO:13) to incorporate a Bam H1 site (underlined) and the downstream primer 5'-GCAAGCTTAGATCTGTGGTCTCATACAGAACTTATAAGATTCCC-3' (SEQ ID NO:14) to incorporate Hind III (underlined) and Bgl II (double underline) sites (5). The fragment was digested with Bam H1 and Hind III and ligated into Bgl II-Hind III digested pcDNA3 (Invitrogen), creating the plasmid pH1.

The IKKγΔ-specific hammerhead ribozyme flanked by the H1 promoter transcription start and termination sites (5) was constructed by annealing synthetic oligonucleotides 5'-GATCCCCTTCCTCC CTGATGAGGCCGAA AGGC-CGAAACCC TCCTTTTTTGGAAA-3' (SEQ ID NO:15) and 5'-AGCTTTTCCAAA AAGGAGGGTTTCGGC CTTTCGGCCTCATCAGGG AGGAAGGG-3' (SEQ ID NO:16). The duplex was then ligated into Bgl II-Hind III restricted pH1. Plasmids were purified by ion exchange chromatography prior to transfection, and all constructions were confirmed by automated sequencing.

The IKKγΔ ribozyme was then tested in 5R cells stably expressing an epitope tagged IKKγΔ. In brief, we observed that transfection of H1-R2 depleted IKKγΔ transcripts after 48 h of transfection (FIG. 8) and depleted IKKγΔ protein 72-110 h after transfection (FIG. 9).

Figure 8:
FIG. 8 is an image showing the abundance of IKKγΔ transcripts in RNA extracted from 5R cells stably expressing IKKγΔ transcript that were transfected with empty plasmid and plasmid expressing IKKγΔ ribozyme.

More particularly, 5R cells stably expressing IKKγΔ transcript were transfected with empty plasmid (pH1), or plasmid expressing IKKγΔ ribozyme (pH1-R2). 48 h later, RNA was extracted and analyzed for abundance of IKKγΔ transcripts by RT-PCR (FIG. 8, top panel), and an equivalent amount of RNA was analyzed for GAPDH abundance by RT-PCR (FIG. 8, bottom panel).

Figure 9:
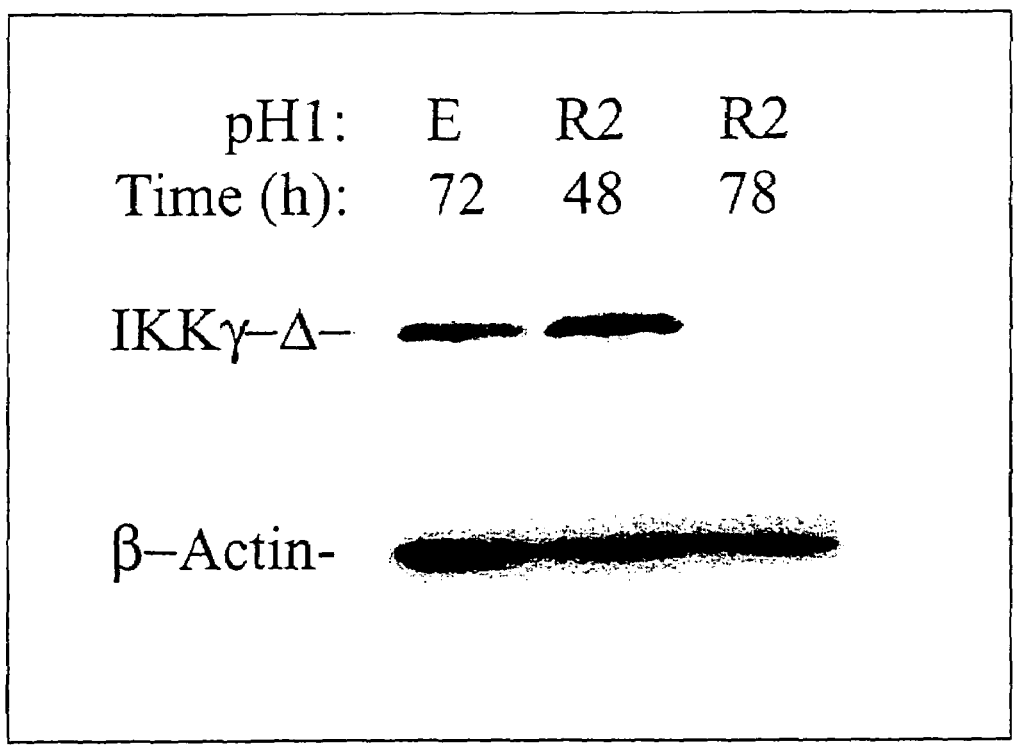
FIG. 9 is an image of a Western immunoblot showing the abundance FLAG IKKγΔ abundance in cytoplasmic extracts from 5R cells stably expressing IKKγΔ transcript that were transfected with empty plasmid and plasmid expressing IKKγΔ ribozyme.

Referring now to FIG. 9, 5R cells stably expressing FLAG IKKγΔ were transfected with pH1 (empty) or pH1-R2 expression plasmids. Cytoplasmic extracts were prepared and FLAG IKKγΔ abundance was detected by Western immunoblot. The top panel of FIG. 9 shows staining with HRP FLAG-M2 antibody. The bottom panel of FIG. 9 shows staining with anti-Rel B (internal control).

These results indicate the ribozyme is efficiently degrading the alternatively spliced transcript and is a potential reagent to modulate IKKγ signaling in cells or tissues.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. An isolated polypeptide having an amino acid sequence comprising SEQ ID NO: 1.

2. An isolated polypeptide according to claim 1, wherein said isolated polypeptide is purified.

3. An isolated polypeptide consisting of an amino acid sequence of SEQ ID NO: 10.

* * * * *